United States Patent
Bovay et al.

(10) Patent No.: US 10,639,109 B2
(45) Date of Patent: May 5, 2020

(54) MICROSURGICAL TOOL FOR ROBOTIC APPLICATIONS

(71) Applicant: Auris Surgical Robotics, Inc., San Carlos, CA (US)

(72) Inventors: Loic Alexandre Bovay, Pully (CH); Travis Schuh, Los Altos, CA (US); Fernando Reyes, Daly City, CA (US); Allen Jiang, Fremont, CA (US)

(73) Assignee: Auris Health, Inc., Redwood City, CA (US)

( * ) Notice: Subject to any disclaimer, the term of this patent is extended or adjusted under 35 U.S.C. 154(b) by 322 days.

(21) Appl. No.: 15/435,790

(22) Filed: Feb. 17, 2017

(65) Prior Publication Data

US 2017/0165011 A1   Jun. 15, 2017

Related U.S. Application Data

(63) Continuation of application No. 15/089,406, filed on Apr. 1, 2016, now abandoned.
(Continued)

(51) Int. Cl.
*A61B 34/30* (2016.01)
*A61B 17/28* (2006.01)
(Continued)

(52) U.S. Cl.
CPC .......... *A61B 34/30* (2016.02); *A61B 17/2804* (2013.01); *A61B 17/2909* (2013.01);
(Continued)

(58) Field of Classification Search
CPC ..... A61B 17/28; A61B 17/2804; A61B 17/29; A61B 2017/2927; A61B 2017/2929;
(Continued)

(56) References Cited

U.S. PATENT DOCUMENTS

| 3,763,860 A | 10/1973 | Clarke |
| 4,040,413 A | 8/1977 | Ohshiro |

(Continued)

FOREIGN PATENT DOCUMENTS

| EP | 1 321 106 | 6/2003 |
| EP | 1 849 423 | 10/2007 |

(Continued)

OTHER PUBLICATIONS

Office action dated Jun. 30, 2016 for U.S. Appl. No. 15/089,406.
Office action dated Nov. 22, 2016 for U.S. Appl. No. 15/089,406.

*Primary Examiner* — Wade Miles
(74) *Attorney, Agent, or Firm* — Knobbe, Martens, Olson & Bear, LLP

(57) ABSTRACT

The disclosed technology includes improved microsurgical tools providing multiple degrees of freedom at the wrist level, including roll, pitch, and grasp DOFs, a tight articulation bending radius, low radial offset, and improved stiffness. Some implementations include an end effector platform moveable along a fixed trajectory on a fictional axle so as not to interfere with a central-axis aligned working channel; a crossed-arm mechanical linkage for articulating an end-effector platform throughout a pitch DOF with an amplified pitch angle; and a partial pulley system to articulate the arms while maximizing pulley radius to shaft diameter, and permitting a constant transmission efficiency to the arms throughout the range of articulation. In some implementations, a tool shaft outer diameter may be smaller than 3 mm; a pitch DOF range may be ±90°, a roll DOF range may be ±180°, and a grasp DOF range may be 30°.

20 Claims, 18 Drawing Sheets

Related U.S. Application Data

(60) Provisional application No. 62/141,817, filed on Apr. 1, 2015.

(51) Int. Cl.
   *A61B 34/00* (2016.01)
   *A61B 17/29* (2006.01)

(52) U.S. Cl.
   CPC .............. *A61B 34/71* (2016.02); *A61B 34/72* (2016.02); *A61B 2017/2912* (2013.01); *A61B 2017/2927* (2013.01); *A61B 2017/2929* (2013.01); *A61B 2034/304* (2016.02); *A61B 2034/305* (2016.02)

(58) Field of Classification Search
   CPC ...... A61B 2017/293; A61B 2017/2939; A61B 34/70; A61B 34/71; A61B 34/72; A61B 2017/2947; A61B 2017/2941
   See application file for complete search history.

(56) References Cited

U.S. PATENT DOCUMENTS

| | | |
|---|---|---|
| 4,198,960 A | 4/1980 | Utsugi |
| 4,470,407 A | 9/1984 | Hussein |
| 4,532,935 A | 8/1985 | Wang et al. |
| 4,685,458 A | 8/1987 | Leckrone |
| 4,747,405 A | 5/1988 | Leckrone |
| 4,898,574 A | 2/1990 | Uchiyama et al. |
| 4,983,165 A | 1/1991 | Loiterman |
| 5,029,574 A | 7/1991 | Shimamura et al. |
| 5,085,659 A | 2/1992 | Rydell |
| 5,196,023 A | 3/1993 | Martin |
| 5,217,465 A | 6/1993 | Steppe |
| 5,308,323 A | 5/1994 | Sogawa et al. |
| 5,318,589 A | 6/1994 | Lichtman |
| 5,325,848 A | 7/1994 | Adams et al. |
| 5,342,381 A | 8/1994 | Tidemand |
| 5,344,395 A | 9/1994 | Whalen et al. |
| 5,353,783 A | 10/1994 | Nakao et al. |
| 5,370,609 A | 12/1994 | Drasler et al. |
| 5,372,124 A | 12/1994 | Takayama et al. |
| 5,411,016 A | 5/1995 | Kume |
| 5,431,649 A | 7/1995 | Mulier et al. |
| 5,441,485 A | 8/1995 | Peters |
| 5,449,356 A | 9/1995 | Walbrink |
| 5,450,843 A | 9/1995 | Moll et al. |
| 5,472,426 A | 12/1995 | Bonati et al. |
| 5,496,267 A | 3/1996 | Drasler |
| 5,501,667 A | 3/1996 | Verduin, Jr. |
| 5,520,684 A | 5/1996 | Imran |
| 5,545,170 A | 8/1996 | Hart |
| 5,562,648 A | 10/1996 | Peterson |
| 5,562,678 A | 10/1996 | Booker |
| 5,572,999 A | 11/1996 | Funda et al. |
| 5,573,535 A | 11/1996 | Viklund |
| 5,613,973 A | 3/1997 | Jackson et al. |
| 5,645,083 A | 7/1997 | Essig et al. |
| 5,653,374 A | 8/1997 | Young et al. |
| 5,658,311 A | 8/1997 | Baden |
| 5,695,500 A | 12/1997 | Taylor et al. |
| 5,697,949 A | 12/1997 | Giurtino et al. |
| 5,710,870 A | 1/1998 | Ohm et al. |
| 5,716,325 A | 2/1998 | Bonutti |
| 5,788,667 A | 8/1998 | Stoller |
| 5,792,165 A | 8/1998 | Klieman |
| 5,797,900 A * | 8/1998 | Madhani .................. B25J 3/04 606/1 |
| 5,810,770 A | 9/1998 | Chin et al. |
| 5,893,869 A | 4/1999 | Barnhart |
| 5,924,175 A | 7/1999 | Lippitt |
| 5,989,230 A | 11/1999 | Frassica |
| 6,071,281 A | 6/2000 | Burnside et al. |
| 6,093,157 A | 7/2000 | Chandrasekaran |
| 6,120,476 A | 9/2000 | Fung et al. |
| 6,120,498 A | 9/2000 | Jani et al. |
| 6,156,030 A | 12/2000 | Neev |
| 6,174,318 B1 | 1/2001 | Bates et al. |
| 6,206,903 B1 | 3/2001 | Ramans |
| 6,183,435 B1 | 6/2001 | Bumbalough et al. |
| 6,322,557 B1 | 11/2001 | Nikolaevich |
| 6,375,635 B1 | 4/2002 | Moutafis |
| 6,394,998 B1 * | 5/2002 | Wallace ................. A61B 34/71 606/1 |
| 6,405,078 B1 | 6/2002 | Moaddeb et al. |
| 6,440,061 B1 | 8/2002 | Wenner et al. |
| 6,508,823 B1 | 1/2003 | Gonon |
| 6,522,906 B1 | 2/2003 | Salisbury et al. |
| 6,577,891 B1 | 6/2003 | Jaross et al. |
| 6,676,668 B2 | 1/2004 | Mercereau et al. |
| 6,685,698 B2 * | 2/2004 | Morley ................. A61B 17/062 606/1 |
| 6,706,050 B1 | 3/2004 | Giannadakis |
| 6,969,385 B2 | 11/2005 | Moreyra |
| 7,282,055 B2 | 10/2007 | Tsuruta |
| 7,288,103 B2 | 10/2007 | Suzuki |
| 7,559,934 B2 | 7/2009 | Teague et al. |
| 7,736,356 B2 | 6/2010 | Cooper et al. |
| 7,819,894 B2 | 10/2010 | Mitsuishi et al. |
| 7,879,070 B2 | 2/2011 | Ortiz et al. |
| 7,963,911 B2 | 6/2011 | Turliuc |
| 8,002,713 B2 | 8/2011 | Heske |
| 8,038,598 B2 | 10/2011 | Khachi |
| 8,092,397 B2 | 1/2012 | Wallace et al. |
| 8,187,173 B2 | 5/2012 | Miyoshi |
| 8,257,303 B2 | 9/2012 | Moll et al. |
| 8,398,674 B2 | 3/2013 | Prestel |
| 8,523,762 B2 | 9/2013 | Miyamoto et al. |
| 8,540,748 B2 * | 9/2013 | Murphy .................. A61B 34/71 606/205 |
| 8,603,077 B2 | 12/2013 | Cooper et al. |
| 8,820,603 B2 | 9/2014 | Shelton et al. |
| 8,882,660 B2 | 11/2014 | Phee et al. |
| 8,945,163 B2 | 2/2015 | Voegele et al. |
| 8,956,280 B2 | 2/2015 | Eversull et al. |
| 9,220,526 B2 | 12/2015 | Conlon |
| 9,259,275 B2 | 2/2016 | Burbank |
| 9,345,456 B2 | 5/2016 | Tsonton et al. |
| 9,460,536 B2 | 10/2016 | Hasegawa et al. |
| 9,504,604 B2 | 11/2016 | Alvarez |
| 9,561,083 B2 | 2/2017 | Yu et al. |
| 9,592,042 B2 | 3/2017 | Titus |
| 9,597,152 B2 | 3/2017 | Schaeffer |
| 9,622,827 B2 | 4/2017 | Yu et al. |
| 9,636,184 B2 | 5/2017 | Lee et al. |
| 9,713,509 B2 | 7/2017 | Schuh et al. |
| 9,727,963 B2 * | 8/2017 | Mintz ..................... A61B 5/061 |
| 9,730,757 B2 * | 8/2017 | Brudniok ............... A61B 34/30 |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 * | 10/2017 | Schuh .................. A61B 34/30 |
| 9,818,681 B2 | 11/2017 | Machida |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 * | 5/2018 | Schuh .................. A61B 34/30 |
| 10,016,900 B1 | 7/2018 | Meyer et al. |
| 10,022,192 B1 | 7/2018 | Ummalaneni |
| 10,136,959 B2 | 11/2018 | Mintz et al. |
| 10,145,747 B1 | 12/2018 | Lin et al. |
| 10,159,532 B1 | 12/2018 | Ummalaneni |
| 10,231,793 B2 | 3/2019 | Romo |
| 10,244,926 B2 | 4/2019 | Noonan et al. |
| 10,285,574 B2 | 5/2019 | Landey et al. |
| 10,299,870 B2 | 5/2019 | Connolly et al. |
| 10,426,559 B2 | 10/2019 | Graetzel et al. |
| 10,434,660 B2 | 10/2019 | Meyer et al. |
| 2002/0019644 A1 | 2/2002 | Hastings |

(56) References Cited

U.S. PATENT DOCUMENTS

| | | |
|---|---|---|
| 2002/0111608 A1 | 8/2002 | Baerveldt |
| 2002/0111621 A1 | 8/2002 | Wallace et al. |
| 2003/0004455 A1 | 1/2003 | Kadziauskas |
| 2003/0040681 A1 | 2/2003 | Ng et al. |
| 2003/0065358 A1 | 4/2003 | Frecker |
| 2003/0109877 A1 | 6/2003 | Morley |
| 2003/0109889 A1 | 6/2003 | Mercereau |
| 2003/0158545 A1 | 8/2003 | Hovda et al. |
| 2003/0208189 A1 | 11/2003 | Payman |
| 2004/0143253 A1 | 7/2004 | Vanney |
| 2004/0153093 A1 | 8/2004 | Donovan |
| 2004/0158261 A1 | 8/2004 | Vu |
| 2004/0186349 A1 | 9/2004 | Ewers |
| 2004/0193146 A1 | 9/2004 | Lee et al. |
| 2004/0210116 A1 | 10/2004 | Nakao |
| 2005/0054900 A1 | 3/2005 | Mawn |
| 2005/0159645 A1 | 7/2005 | Bertolero |
| 2005/0240178 A1 | 10/2005 | Morley et al. |
| 2005/0261705 A1 | 11/2005 | Gist |
| 2006/0015133 A1 | 1/2006 | Grayzel |
| 2006/0058813 A1 | 3/2006 | Teague |
| 2006/0116693 A1 | 6/2006 | Weisenburgh |
| 2006/0135963 A1 | 6/2006 | Kick |
| 2006/0156875 A1 | 7/2006 | McRury et al. |
| 2006/0189891 A1 | 8/2006 | Waxman et al. |
| 2007/0016164 A1 | 1/2007 | Dudney et al. |
| 2007/0027443 A1 | 2/2007 | Rose |
| 2007/0027534 A1 | 2/2007 | Bergheim |
| 2007/0032906 A1 | 2/2007 | Sutherland et al. |
| 2007/0106304 A1 | 5/2007 | Hammack |
| 2007/0135803 A1 | 6/2007 | Belson |
| 2007/0208375 A1* | 9/2007 | Nishizawa ............ A61B 17/29 606/205 |
| 2007/0213668 A1 | 9/2007 | Spitz |
| 2007/0239178 A1 | 10/2007 | Weitzner et al. |
| 2007/0250111 A1 | 10/2007 | Lu |
| 2007/0299427 A1 | 12/2007 | Yeung et al. |
| 2008/0015566 A1 | 1/2008 | Livneh |
| 2008/0021440 A1 | 1/2008 | Solomon |
| 2008/0033467 A1 | 2/2008 | Miyamoto et al. |
| 2008/0046122 A1 | 2/2008 | Manzo et al. |
| 2008/0065111 A1 | 3/2008 | Blumenkranz |
| 2008/0125698 A1 | 5/2008 | Greg et al. |
| 2008/0187101 A1 | 8/2008 | Gertner |
| 2008/0196533 A1 | 8/2008 | Bergamasco et al. |
| 2008/0228104 A1 | 9/2008 | Uber et al. |
| 2009/0012507 A1 | 1/2009 | Culbertson et al. |
| 2009/0036900 A1 | 2/2009 | Moll |
| 2009/0043305 A1 | 2/2009 | Brodbeck |
| 2009/0082634 A1 | 3/2009 | Kathrani et al. |
| 2009/0088774 A1 | 4/2009 | Swarup et al. |
| 2009/0105723 A1 | 4/2009 | Dillinger |
| 2009/0131885 A1 | 5/2009 | Akahoshi |
| 2009/0161827 A1 | 6/2009 | Gertner et al. |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299352 A1 | 12/2009 | Zerfas |
| 2010/0004642 A1 | 1/2010 | Lumpkin |
| 2010/0010504 A1 | 1/2010 | Simaan et al. |
| 2010/0011901 A1 | 1/2010 | Burbank |
| 2010/0082017 A1 | 4/2010 | Zickler |
| 2010/0179632 A1 | 7/2010 | Bruszewski et al. |
| 2010/0204605 A1 | 8/2010 | Blakley |
| 2010/0204646 A1 | 8/2010 | Plicchi et al. |
| 2010/0217235 A1 | 8/2010 | Thorstenson |
| 2010/0225209 A1 | 9/2010 | Goldberg |
| 2010/0228249 A1 | 9/2010 | Mohr |
| 2010/0312141 A1 | 12/2010 | Keast et al. |
| 2010/0331858 A1 | 12/2010 | Simaan et al. |
| 2011/0015483 A1 | 1/2011 | Barbagli |
| 2011/0071541 A1 | 3/2011 | Prisco et al. |
| 2011/0071543 A1 | 3/2011 | Prisco et al. |
| 2011/0106146 A1* | 5/2011 | Jeong ..................... A61B 17/29 606/208 |
| 2011/0125165 A1 | 5/2011 | Simaan et al. |
| 2011/0152880 A1 | 6/2011 | Alvarez et al. |
| 2011/0160713 A1 | 6/2011 | Neuberger |
| 2011/0167611 A1 | 7/2011 | Williams |
| 2011/0213362 A1* | 9/2011 | Cunningham ..... A61B 18/1445 606/41 |
| 2011/0224660 A1 | 9/2011 | Neuberger et al. |
| 2011/0238064 A1 | 9/2011 | Williams et al. |
| 2011/0257641 A1 | 10/2011 | Hastings et al. |
| 2011/0276085 A1* | 11/2011 | Krzyzanowski ....... A61B 10/06 606/208 |
| 2011/0313343 A1 | 12/2011 | Milutinovic et al. |
| 2012/0069167 A1 | 3/2012 | Liu et al. |
| 2012/0253277 A1 | 4/2012 | Tah et al. |
| 2012/0138586 A1 | 6/2012 | Webster et al. |
| 2012/0209315 A1* | 8/2012 | Amat Girbau ......... A61B 34/70 606/207 |
| 2012/0232342 A1 | 9/2012 | Reydel |
| 2012/0253332 A1 | 10/2012 | Moll |
| 2012/0259320 A1 | 10/2012 | Loesel et al. |
| 2012/0296318 A1 | 11/2012 | Wellhofer et al. |
| 2013/0006144 A1 | 1/2013 | Clancy |
| 2013/0035537 A1 | 2/2013 | Wallace et al. |
| 2013/0066136 A1 | 3/2013 | Palese et al. |
| 2013/0085442 A1 | 4/2013 | Shtul et al. |
| 2013/0085486 A1 | 4/2013 | Boutoussov et al. |
| 2013/0096422 A1 | 4/2013 | Boctor |
| 2013/0096574 A1 | 4/2013 | Kang et al. |
| 2013/0110042 A1 | 5/2013 | Humphreys |
| 2013/0110107 A1 | 5/2013 | Smith et al. |
| 2013/0116716 A1 | 5/2013 | Bahls et al. |
| 2013/0190796 A1 | 7/2013 | Tilson et al. |
| 2013/0225997 A1 | 8/2013 | Dillard et al. |
| 2013/0253267 A1 | 9/2013 | Collins |
| 2013/0303876 A1 | 11/2013 | Gelfand et al. |
| 2013/0310819 A1 | 11/2013 | Neuberger et al. |
| 2013/0345686 A1 | 12/2013 | Brown |
| 2014/0005681 A1 | 1/2014 | Gee et al. |
| 2014/0039681 A1 | 2/2014 | Bowling |
| 2014/0046308 A1 | 2/2014 | Bischoff |
| 2014/0051985 A1 | 2/2014 | Fan et al. |
| 2014/0058365 A1 | 2/2014 | Bille |
| 2014/0058404 A1 | 2/2014 | Hammack |
| 2014/0058428 A1 | 2/2014 | Christopher |
| 2014/0100445 A1 | 4/2014 | Stenzel |
| 2014/0142591 A1 | 5/2014 | Alvarez et al. |
| 2014/0163318 A1 | 6/2014 | Swanstrom |
| 2014/0194859 A1 | 7/2014 | Ianchulev |
| 2014/0194905 A1* | 7/2014 | Kappel ................. A61B 17/062 606/144 |
| 2014/0243849 A1 | 8/2014 | Saglam |
| 2014/0275956 A1 | 9/2014 | Fan |
| 2014/0276723 A1 | 9/2014 | Parihar |
| 2014/0276956 A1 | 9/2014 | Crainich |
| 2014/0309649 A1 | 10/2014 | Alvarez et al. |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0051592 A1 | 2/2015 | Kintz |
| 2015/0101442 A1 | 4/2015 | Romo |
| 2015/0119638 A1 | 4/2015 | Yu et al. |
| 2015/0127045 A1 | 5/2015 | Prestel |
| 2015/0164522 A1 | 6/2015 | Budiman |
| 2015/0164594 A1 | 6/2015 | Romo et al. |
| 2015/0164596 A1 | 6/2015 | Romo |
| 2015/0201917 A1 | 7/2015 | Snow |
| 2015/0202085 A1 | 7/2015 | Lemonis |
| 2015/0209965 A1 | 7/2015 | Low et al. |
| 2015/0314110 A1 | 11/2015 | Park |
| 2015/0335480 A1 | 11/2015 | Alvarez et al. |
| 2016/0001038 A1 | 1/2016 | Romo et al. |
| 2016/0022289 A1 | 1/2016 | Wan |
| 2016/0022466 A1 | 1/2016 | Pedtke |
| 2016/0030073 A1 | 2/2016 | Lsakov |
| 2016/0045208 A1 | 2/2016 | Ciulla |

(56) References Cited

U.S. PATENT DOCUMENTS

| | | |
|---|---|---|
| 2016/0051318 A1 | 2/2016 | Manzo et al. |
| 2016/0066935 A1 | 3/2016 | Nguyen et al. |
| 2016/0158490 A1 | 6/2016 | Leeflang |
| 2016/0183841 A1 | 6/2016 | Duindam et al. |
| 2016/0199984 A1 | 7/2016 | Lohmeier et al. |
| 2016/0235495 A1 | 8/2016 | Wallace et al. |
| 2016/0249932 A1 | 9/2016 | Rogers et al. |
| 2016/0270865 A1 | 9/2016 | Landey et al. |
| 2016/0279394 A1 | 9/2016 | Moll et al. |
| 2016/0287279 A1 | 10/2016 | Bovay et al. |
| 2016/0296294 A1 | 10/2016 | Moll et al. |
| 2016/0303743 A1 | 10/2016 | Rockrohr |
| 2016/0331358 A1 | 11/2016 | Gordon |
| 2016/0367324 A1 | 12/2016 | Sato et al. |
| 2016/0374541 A1 | 12/2016 | Agrawal et al. |
| 2017/0007337 A1 | 1/2017 | Dan |
| 2017/0049471 A1 | 2/2017 | Gaffney et al. |
| 2017/0065227 A1 | 3/2017 | Marrs |
| 2017/0065364 A1 | 3/2017 | Schuh et al. |
| 2017/0065365 A1 | 3/2017 | Schuh |
| 2017/0095234 A1 | 4/2017 | Prisco et al. |
| 2017/0095295 A1 | 4/2017 | Overmyer |
| 2017/0100199 A1 | 4/2017 | Yu et al. |
| 2017/0119413 A1 | 5/2017 | Romo |
| 2017/0119481 A1 | 5/2017 | Romo et al. |
| 2017/0172553 A1 | 6/2017 | Chaplin |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0290631 A1 | 10/2017 | Lee et al. |
| 2017/0319289 A1 | 11/2017 | Neff et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0000563 A1 | 1/2018 | Shanjani et al. |
| 2018/0025666 A1 | 1/2018 | Ho et al. |
| 2018/0177556 A1 | 6/2018 | Noonan et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0105776 A1 | 4/2019 | Ho et al. |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan |
| 2019/0298460 A1 | 10/2019 | Al-Jadda |
| 2019/0298465 A1 | 10/2019 | Chin |
| 2019/0314616 A1 | 10/2019 | Moll et al. |
| 2019/0328213 A1 | 10/2019 | Landey et al. |

FOREIGN PATENT DOCUMENTS

| | | |
|---|---|---|
| JP | 2005-270464 | 10/2005 |
| WO | WO 11/161218 | 12/2011 |
| WO | WO 13/107468 | 7/2013 |
| WO | WO 13/130895 | 9/2013 |
| WO | WO 17/114855 | 7/2017 |
| WO | WO 18/069679 | 4/2018 |

* cited by examiner

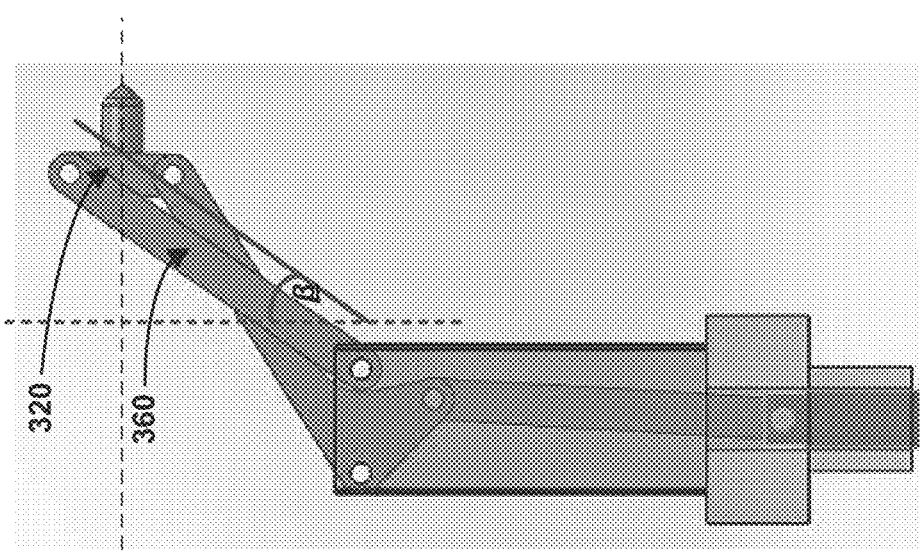
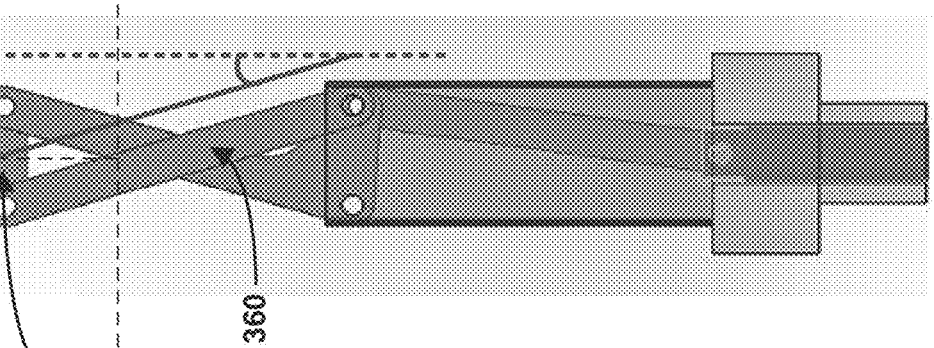
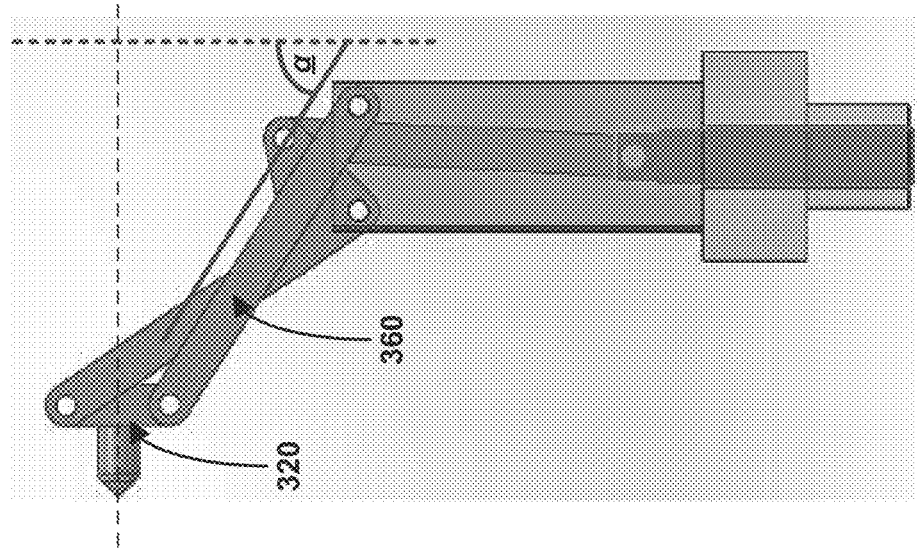

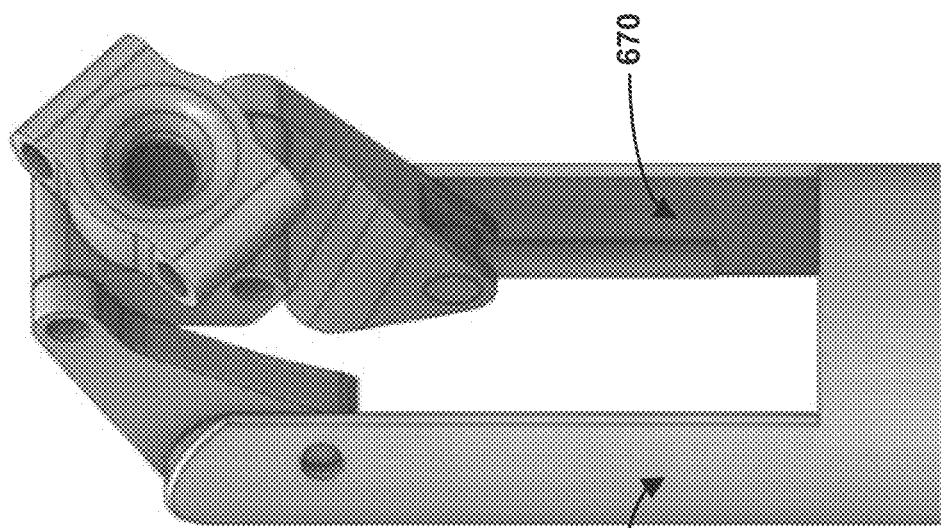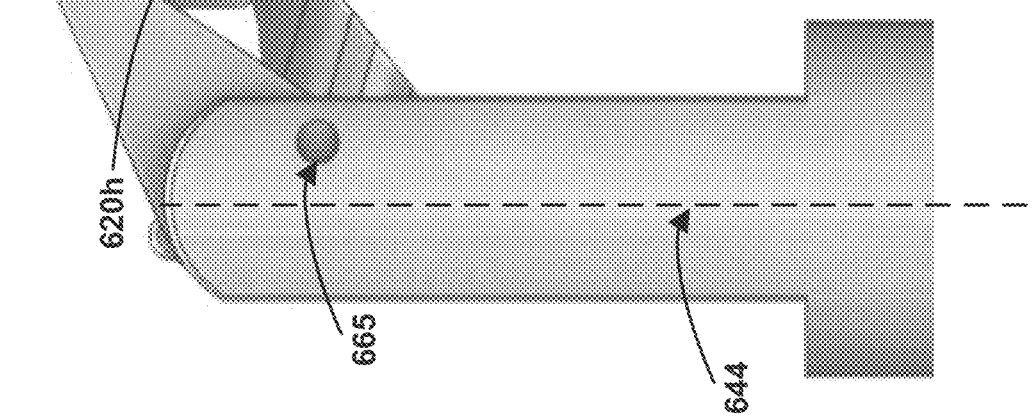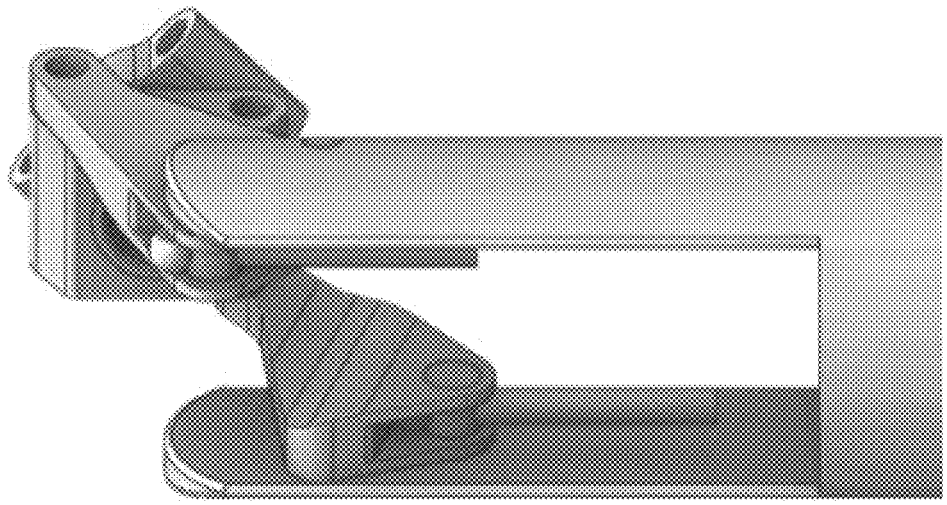

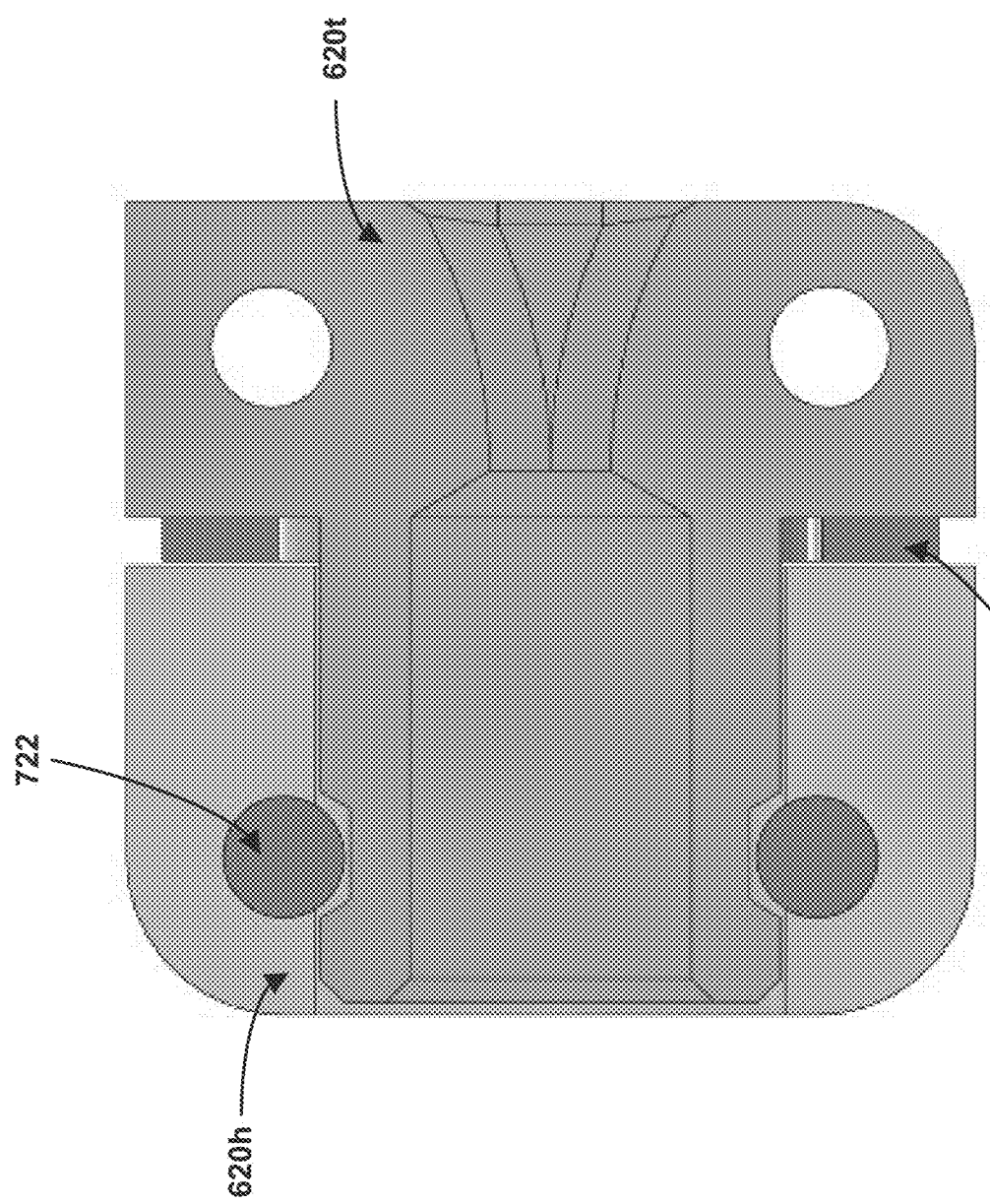

962

962

FIG. 15A
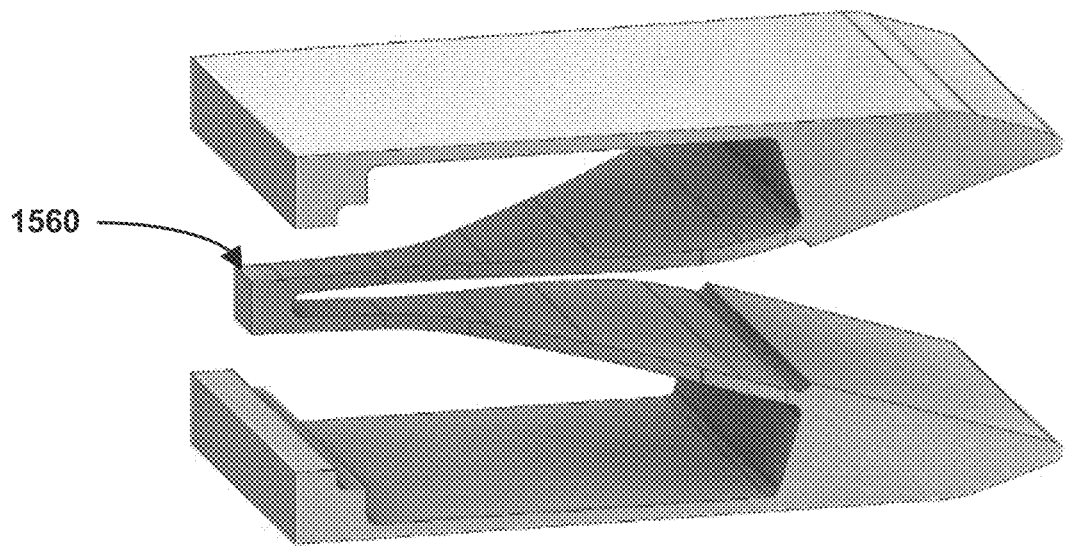
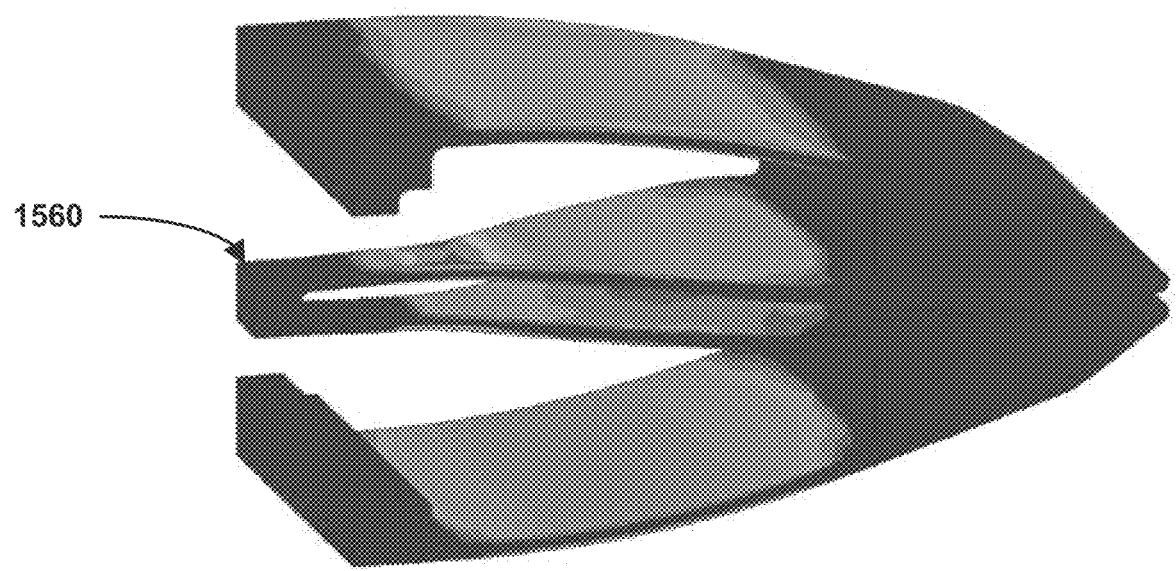
FIG. 15B

MICROSURGICAL TOOL FOR ROBOTIC APPLICATIONS

CROSS-REFERENCE

This application is a continuation of U.S. patent application Ser. No. 15/089,406, filed Apr. 1, 2016, which claims the benefit of U.S. Provisional Application No. 62/141,817, filed Apr. 1, 2015, which applications are incorporated herein by reference.

BACKGROUND

Surgeries can be long and tedious procedures requiring intense focus and high accuracy from a surgeon. To help surgeons stay at the best of their abilities, it is important to consider a surgeon's comfort and keep fatigue to a minimum during a surgical procedure. To this end, robots can help sustain a surgeon's functionality and performance over extended periods of time. Moreover, robots may provide effective tools to increase the surgeon's capability and efficiency beyond levels sustainable with manual tools.

Some advantages provided by robotics in surgery include: allowing the surgeon to operate more comfortably to lessen strain and tiredness; providing better visualization of an operating area; allowing manipulation of tools exceeding manual dexterity; providing greater steadiness and accuracy; enabling teleoperation; and facilitating shorter procedure times, thus lowering costs for providers and patients. Some of these advantages are especially important for successful minimal invasive surgery (MIS) and microsurgery, where dexterity, access, and good vision are paramount.

Conventional robots and surgical tools, however, do not effectively maximize these benefits particularly when scaled down to sizes suitable for MIS and microsurgery. For example, some conventional gear-based transmissions have machinability limits. Moreover, gears may interfere with a working channel of a tool where space is at a premium. Conventional pulley-based systems may suffer from a diminishing bending radius when scaled down, and spring-flexure-based systems often lack stiffness. Even tools relying on simple elastic properties of materials may experience exacerbated fatigue issues.

SUMMARY

Some or all of the above limitations may be addressed by many implementations of the technology disclosed herein. Example implementations include improved tools and devices suitable for MIS and microsurgery robotic applications. Some implementations provide for multiple degrees of freedom ("DOF") at the wrist level, including roll, pitch, and grasp DOFs, while maintaining a tight articulation bending radius.

According to an example implementation, a microsurgical tool is provided. The microsurgical tool may comprise an elongated body having a centerline and outer diameter at a distal end of the elongated body. The microsurgical tool may further comprise a platform moveably coupled to the distal end of the elongated body. The microsurgical tool may yet further comprise an end effector operatively coupled to the platform and being articulable in at least three degrees of freedom, including a pitch degree of freedom up to a pitch angle of at least ±90°. The microsurgical tool may also have a ratio of the outer diameter of the elongated body, to a radial offset of the end effector to the centerline the elongated body, of at least 0.65.

In an example implementation, the ratio of the outer diameter to the radial offset may be at least 0.83. The microsurgical tool may further comprise a torque coil or flexible tube disposed within the elongated body to transmit torque for articulating the end effector in a roll degree of freedom. The end effector may be repeatedly or infinitely articulable in a roll degree of freedom. The end effector may also be at least one of a grasper, a gripper, forceps, or scissors.

In another example implementation, the microsurgical may also comprise an actuation tendon disposed within the elongated body. The actuation tendon may be tensionable to actuate the end effector in a grip degree of freedom. The microsurgical tool may also comprise a torque coil disposed within the elongated body to transmit torque for articulating the end effector in a roll degree of freedom with the actuation tendon being disposed within the torque coil.

In yet another example implementation, the end effector may also comprise a deformable grasper. The end effector may also comprise a unilateral grasper, or a grasper with at least one fixed jaw and one moving jaw. Alternatively, the end effector may comprise at least two opposing jaws articulable to open to an angle of at least about 30° relative to each other.

According to another example implementation, a microsurgical tool is provided. The microsurgical tool may comprise an elongated body having a proximal end and a distal end. The microsurgical tool may further comprise a platform operatively coupled to an end effector. The microsurgical tool may yet further comprise a first arm operatively coupled to a first proximal hinge and a first distal hinge, and a second arm operatively coupled to a second proximal hinge and a second distal hinge. The first proximal hinge and the second proximal hinge may be coupled to the distal end of the elongated body and the first distal hinge and the second distal hinge may be coupled to the platform. The first arm and the second arm may be moveable to articulate the end effector in a pitch degree of freedom.

In an example implementation, the end effector may be articulable in a pitch degree of freedom up to a pitch angle of at least about ±90°. The microsurgical tool may comprise a mechanical link for amplifying a pitch angle of the platform by a factor A relative to a pitch angle of the first arm or second arm.

In another example implementation, the first proximal hinge and the second proximal hinge may be coupled to the distal end of the elongated body and the first distal hinge and the second distal hinge may be coupled to the platform such that the first arm and the second arm are crossed. The elongated body may have a centerline and the first proximal hinge may be offset from the centerline. The microsurgical tool may further comprise a mechanical link for moving the first arm with a constant transmission efficiency between the mechanical link and first arm throughout a range of movement of the first arm.

In yet another example implementation, the microsurgical tool may further comprise a first tendon coupled to the first arm and tensionable to move the first arm. The first arm may be coupled to a first pulley. An axis of the pulley may be concentric with the first proximal hinge. The first pulley may be a partial pulley such that a radius of the pulley not in contact with the first tendon is smaller than a radius of the pulley that is in contact with the first tendon, or such that a profile of the pulley is a sector rather than a full circle. In some implementations, the first pulley may fit within a profile of the elongated body.

Other implementations, features, and aspects of the disclosed technology are described in detail herein and are considered a part of the claimed disclosed technology. Other implementations, features, and aspects may be understood with reference to the following detailed description, accompanying drawings, and claims.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosed technology are set forth with particularity in the appended claims. A better understanding of the features and advantages of the present technology will be obtained by reference to the following detailed description that sets forth illustrative implementations, in which the principles of the technology are utilized, and the accompanying drawings of which:

FIGS. 3A, 3B, and 3C depict illustrations of the platform 320 being articulated from −90° to +90° using a crossed-arm linkage, according to an example implementation.

FIGS. 6A, 6B, and 6C depict illustrations of another crossed-arm linkage 600, according to an example implementation.

FIG. 7 depicts an illustration of the platform assembly 700, according to an example implementation.

FIGS. 15A and 15B depict illustrations of a deformable grasper, according to an example implementation.

DETAILED DESCRIPTION

Figure 1:
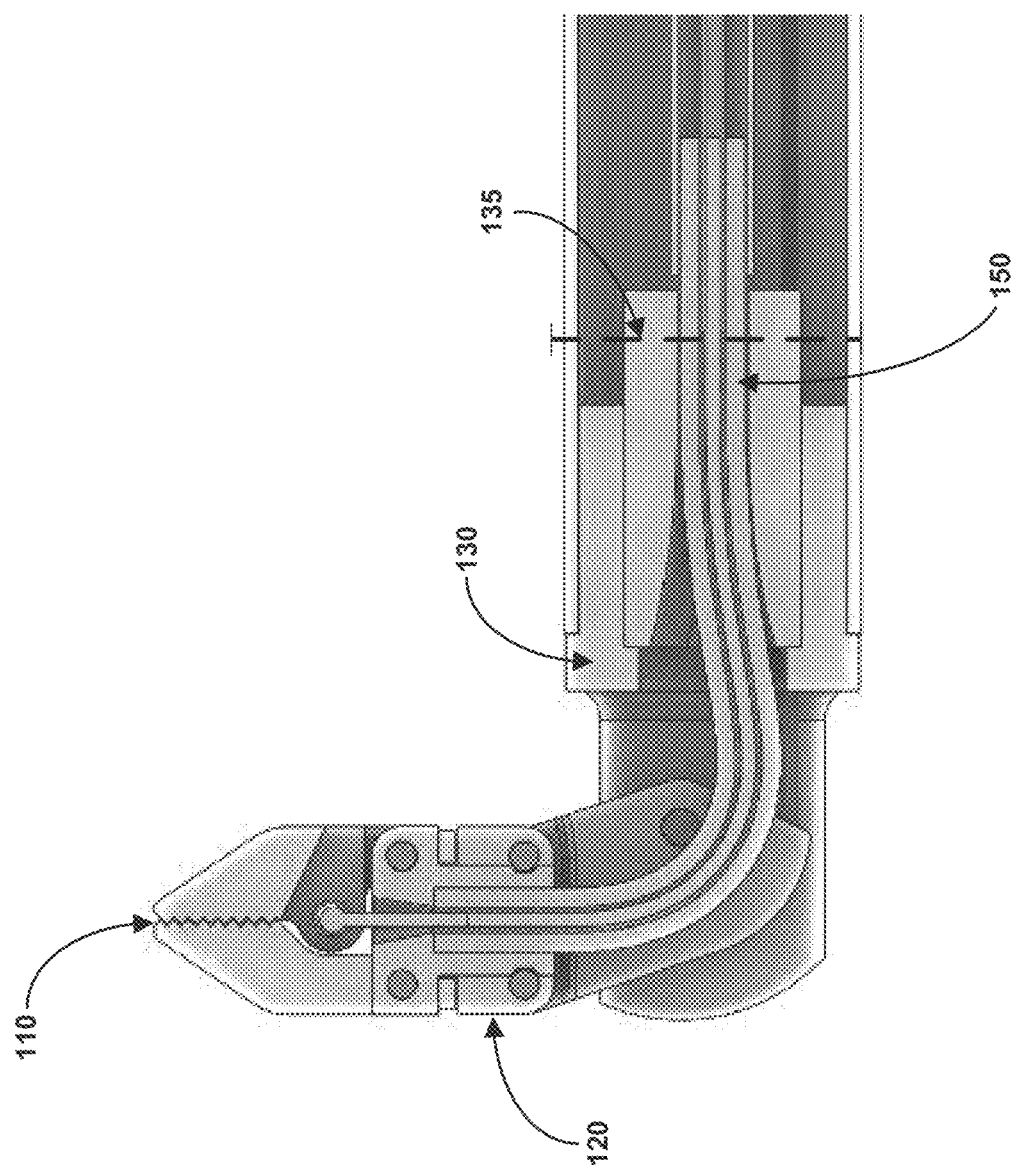
FIG. 1 depicts an illustration of a microsurgery tool 100, according to an example implementation.

To facilitate an understanding of the principles and features of implementations of the disclosed technology, various example implementations are explained below. Although some implementations of the disclosed technology are explained in detail, other implementations are contemplated. Further, in describing example implementations, specific terminology will be resorted to for the sake of clarity. It is not intended that the disclosed technology be limited in scope to the details of construction and arrangement of components set forth in the following description or illustrated in the drawings. Rather, the disclosed technology is capable of other implementations and of being practiced or carried out in various ways.

Throughout the specification and the claims, the following terms take at least the meanings explicitly associated herein, unless the context clearly dictates otherwise. The term "coupled" means that one function, feature, structure, or characteristic is directly or indirectly joined to or in communication with another function, feature, structure, or characteristic. Relational terms such as "first" and "second," and the like may be used solely to distinguish one entity or action from another entity or action without necessarily requiring or implying any actual such relationship or order between such entities or actions. The term "or" is intended to mean an inclusive "or." Further, the terms "a," "an," and "the" are intended to mean one or more unless specified otherwise or clear from the context to be directed to a singular form. The term "include" and its various forms are intended to mean including but not limited to.

Although example implementations are described herein in the context of robotic applications, one of skill in the art will appreciate that the disclosed technology may be applicable to manually operated tools and surgeries. Moreover, although various crossed-arm linkages are described in detail, one of skill in the art will appreciate that other mechanical links and actuators may be used in place of or in addition to parts and components described herein.

Many implementations of the disclosed technology include improved microsurgical tools, instruments, and devices for robotic applications. Some implementations provide multiple degrees of freedom ("DOF") at the wrist level, including roll, pitch, and grasp DOFs, a tight articulation bending radius, low radial offset, or improved stiffness. These features may afford various benefits. For example, a reduced outer diameter can promote less scarring and quicker recovery; compact articulations and a tight bending radius may aid working in confined spaces; a versatile platform can increase the capabilities of the surgical tool; multiple DOF and high ranges of articulation can improve dexterity and reachability; a stiff tool shaft and small radial offset may preserve the line of sight of operation; and torsional stiffness can reduce backlash and improve consistency.

To these ends, the present disclosure introduces a robust but versatile platform assembly for end-effector coupling, the platform being moveable along a fixed trajectory on a fictional axle so as not to interfere with a center-axis-aligned working channel; a crossed-arm mechanical linkage for articulating an end-effector platform throughout a pitch DOF with an amplified pitch angle; and a partial pulley system to articulate the linkage arms while maximizing pulley radius to tool shaft diameter, and permitting a constant transmission efficiency to the arms throughout the range of articulation.

According to many implementations, a tool shaft outer diameter may be smaller than 3 mm; and at the wrist-level, a pitch DOF range may be at least ±90°, a roll DOF range may be at least +180°, and a grasp DOF range may be at least 30°. The platform may be operatively coupled to one or more end effectors, including but not limited to, graspers, bipolar grippers, biopsy graspers, needle drivers, irrigation and suction pipes, needles, lasers, and force sensors.

Referring now to the figures, in which like reference numerals represent like parts throughout the views, these and other features of the disclosed technology will be described in detail.

FIG. 1 depicts an illustration of a microsurgery tool 100, according to an example implementation. As shown in FIG. 1, the tool may comprise a shaft 130 or elongated body, and a platform 120 or platform assembly moveably coupled to an end of the shaft. The platform may support or be coupled to an end effector 110 such as a grasper, as shown. The platform or end effector may be articulable at a "wrist" of the tool near the end of the body. The shaft may have an outer diameter 135, and an inner diameter circumscribing a working channel 150 of the tool. The inner channel may contain tendons, actuators, or other mechanisms for articulating the platform or end effector.

MIS procedures typically rely on small punctures to access an operation area. It can be beneficial to keep these punctures as small as possible to shorten hospital stay and scarring. A related challenge is augmenting dexterity. It can be beneficial to have more DOFs at the wrist level of a tool in order to reach more areas once inside a patient's body. Increased dexterity and reduced size are often tradeoffs. Many implementations of the disclosed technology, however, seek to maximize these benefits, by reducing a tool outer diameter while providing improved capability, such as multiple DOF and increased grip strength.

Accordingly, a significant design objective was to provide multiple DOF at robust ranges while minimizing or reducing the surgical tool shaft and radial offset, which correspond to the bending radius. As used herein, the radial offset may refer to how far the end effector or another tip of the tool radially extends from a shaft axis.

According to many implementations, mechanical links may be used to transmit power to the platform 120 or end effector 110. The type of links or linkage geometry may be configured to minimize or reduce backlash and to maximize or improve a stiffness of transmission. These two features are often significant in providing good control and feeling when using a microsurgical tool.

Figure 2:
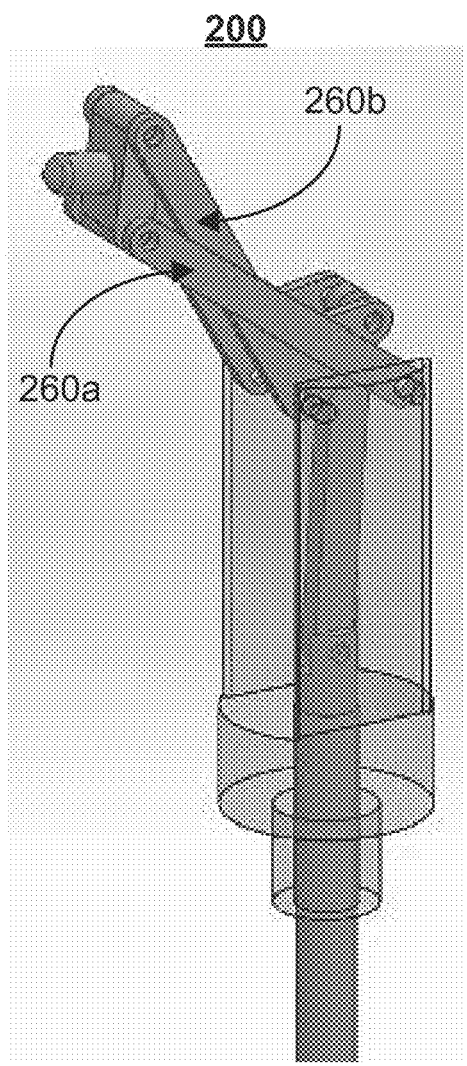
FIG. 2 depicts an illustration of a crossed-arm linkage 200 for articulating a platform, according to an example implementation.

FIG. 2 depicts an illustration of a crossed-arm linkage 200 for articulating a platform, according to an example implementation. To articulate the platform in a pitch DOF, a compliant hinge or linkage was provided based on crossing arms 260a and 260b. In some implementations, the linkage may act as an amplifier between the pitch angle of the arms and the platform or end effector. For example, when the arms travel a range of $R_{arms}$ degrees, the platform may move over a range of $A \cdot R_{arms}$ with A being the amplification factor. This amplification factor may be tuned by altering the geometrical properties of the linkage.

FIGS. 3A, 3B, and 3C depict illustrations of the platform 320 being articulated from −90° to +90° using a crossed-arm linkage, according to an example implementation. In FIG. 3A, the platform is at an angle of −90° and a first arm 310 is at an angle α of −58°. In FIG. 3C, the platform is at an angle of +90° and the first arm 310 is at an angle α of −33°. Thus, although the platform traverses a range of 180°, the arm may travel only from a range of 91°.

Figure 4:
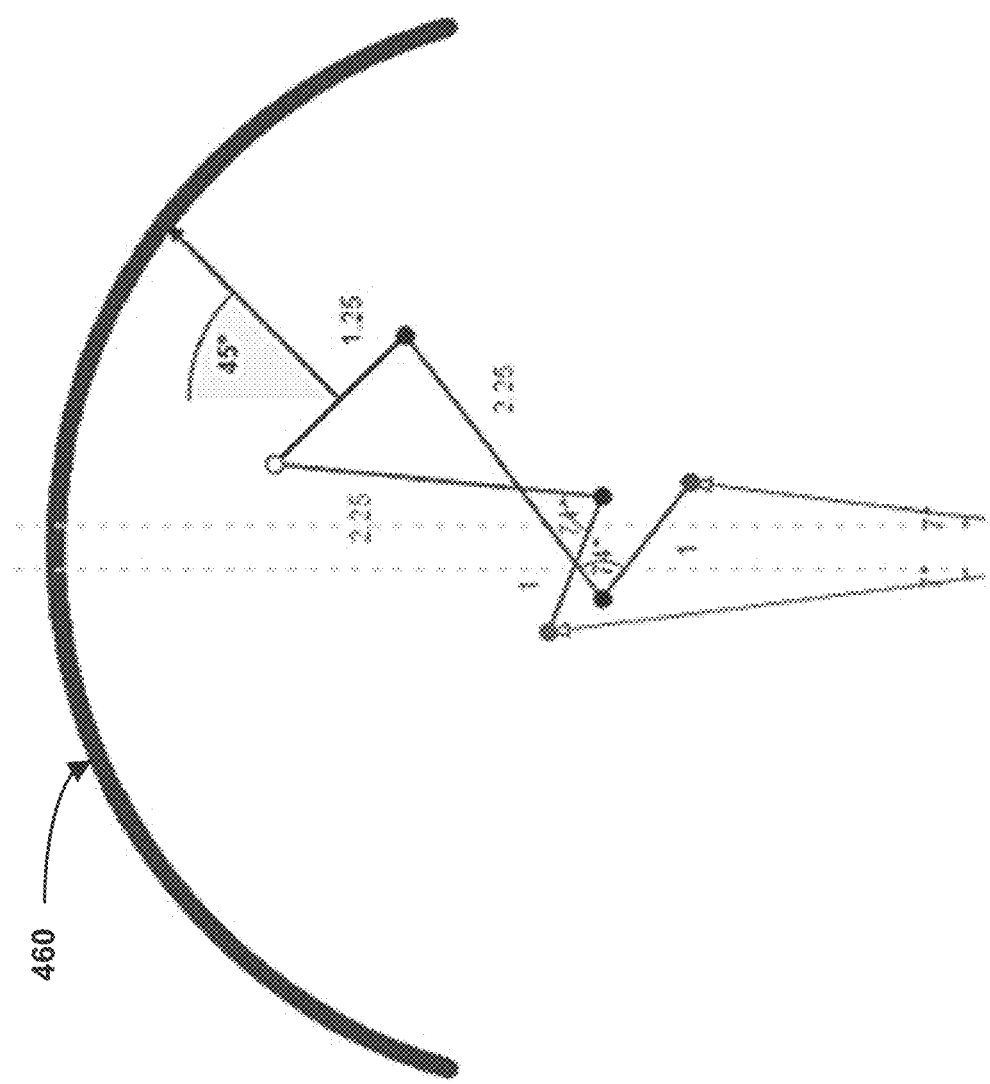
FIG. 4 depicts an illustration of a geometrical model 400 of the articulation 460 of the crossed-arm linkage 200, according to an example implementation.

FIG. 4 depicts an illustration of a geometrical model 400 of the articulation 460 of the crossed-arm linkage 200, according to an example implementation. Even taking into account a change in pitch angle of both arms (e.g., by averaging the pitch angles of the first and second arms) the clear reduction in required arm rotation range permitted by the crossed-arm linkage may reduce the shaft and radial offset of the tool.

FIGS. 6A, 6B, and 6C depict illustrations of another crossed-arm linkage 600, according to an example implementation. To accommodate a roll DOF, a second crossed-arm linkage was provided that opens up a center channel of the tool between base walls 670 for a roll actuation mechanism. In order to free up space around the central axis, two of the four arms were removed over linkage 200 and a two-part platform assembly was provided that would allow a tip 620t of the assembly to rotate freely inside of the head 620h. As shown in FIG. 6B, a respective proximal hinge 665 of the arms may be offset from a centerline 644 of the shaft.

FIG. 7 depicts an illustration of the platform assembly 700, according to an example implementation. In some implementations, two pins may interface 722 with a grove in the tip 620b to hold it axially while allowing rotation. A washer 724 may be added to provide a smooth surface to limit friction when the parts are axially pushed together. When the parts are axially pulled apart, the pin and grove interface may be relied on to provide smooth rotation. Varying washer thickness may help achieve an improved balance between backlash and friction.

With the center axis opened up, various mechanical mechanism were evaluated for adding a roll DOF at the tip. According to many implementations, a torque coil may be used to transmit torque for articulating a tip of the platform assembly or an end effector in a roll DOF. In another implementation, a laser-cut highly flexible tube may be used.

Figure 13C:
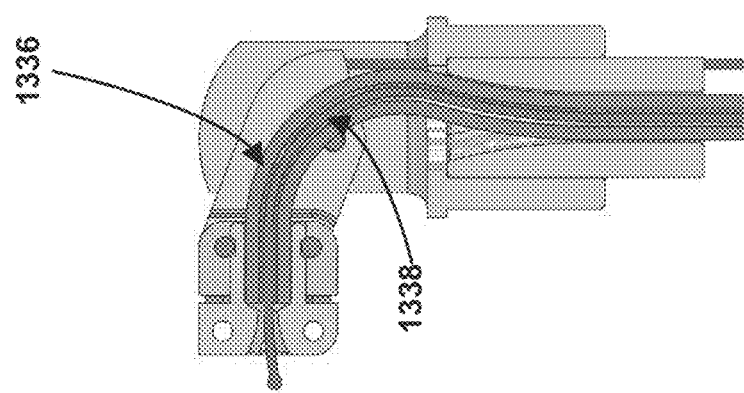
FIG. 13C depicts an illustration of a torque coil with a greater bending radius than the microsurgical tool, according to an example implementation.
Figure 13B:
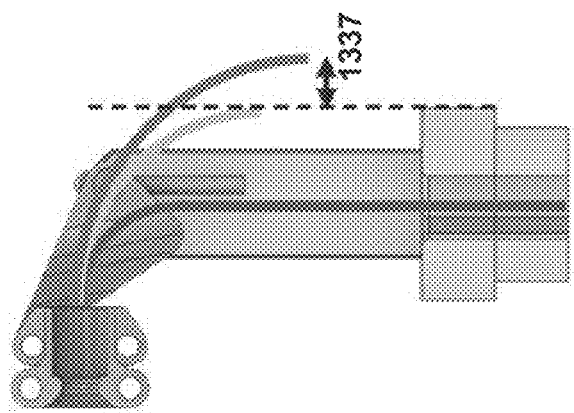
FIG. 13B depicts an illustration of torque coil overshoot, according to an example implementation.
Figure 13A:
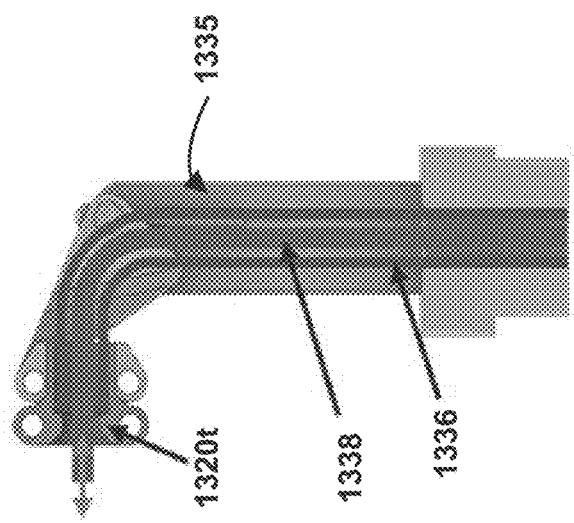
FIG. 13A depicts an illustration of a torque coil actuation mechanism, according to an example implementation.

FIG. 13A depicts an illustration of a torque coil actuation mechanism, according to an example implementation. As shown in FIG. 13A, a torque coil 1336 may be disposed within an inner diameter of the shaft 1335.

FIG. 13A depicts an illustration of a torque coil actuation mechanism, according to an example implementation. As shown in FIG. 13A, a torque coil 1336 may be disposed within an inner diameter of the shaft 1335. In some implementations, a tendon or other actuation mechanisms may be further disposed within the torque coil itself, for example, tendon 1320 for opening and closing a grasper, as shown in FIGS. 13A and 13C.

It was experimentally determined that two-layer torque coils as used in these implementations may transmit torque in an asymmetrical way, whereas three-layer torque coils may transmit torque symmetrically in both directions. Each of the tested specimens also surpassed the flexure grasper torque.

FIG. 13B depicts an illustration of torque coil overshoot, according to an example implementation. It was determined that a yield bending radius of the torque coil may be a limiting factor to the bending radius of the tool. However, as shown in FIG. 13B, open space in the back of the arm crossed arm assembly may allow for the torque coil to have an overshoot 1337. Accordingly, in some implementations, the tool may have a tighter bending radius than the torque coil, as shown in FIG. 13C.

Figure 8:
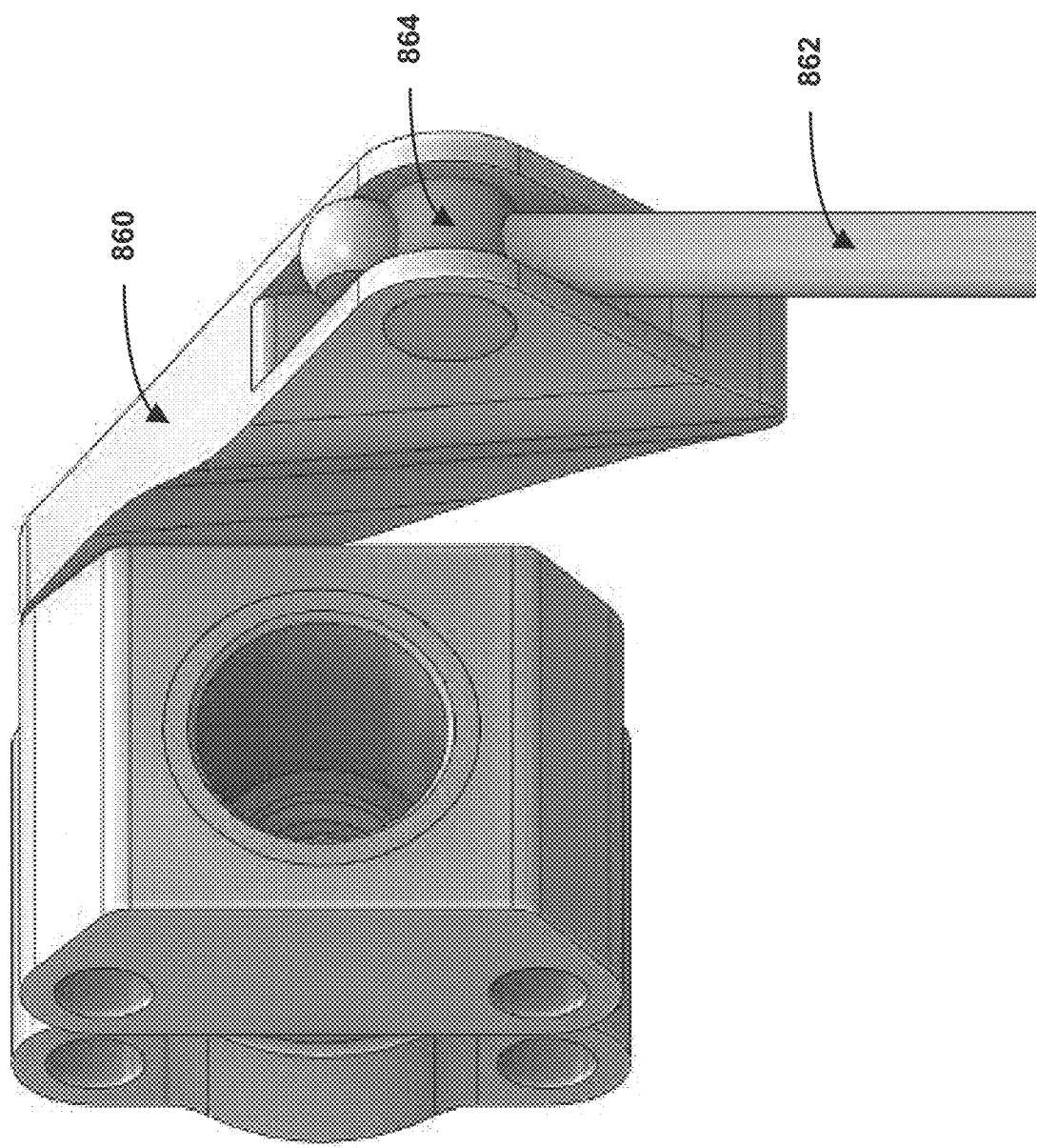
FIG. 8 depicts an illustration of a pull-wire attachment for articulating an arm, according to an example implementation.

FIG. 8 depicts an illustration of a pull-wire attachment for articulating an arm, according to an example implementation. In some implementations, actuation of the arms of the tool may control the head pitch angle. As shown in FIG. 8, a pull wire 862 may be attached to an arm 860 with a pierced pin 864 and tensioned to make the arm rotate.

In some implementations, the pierced pen 864 attachment implemented with linkage 600 may result in a device with relatively thin walls around the pierced pin. This lack of thickness could limit the scalability of the tool.

Figure 5:
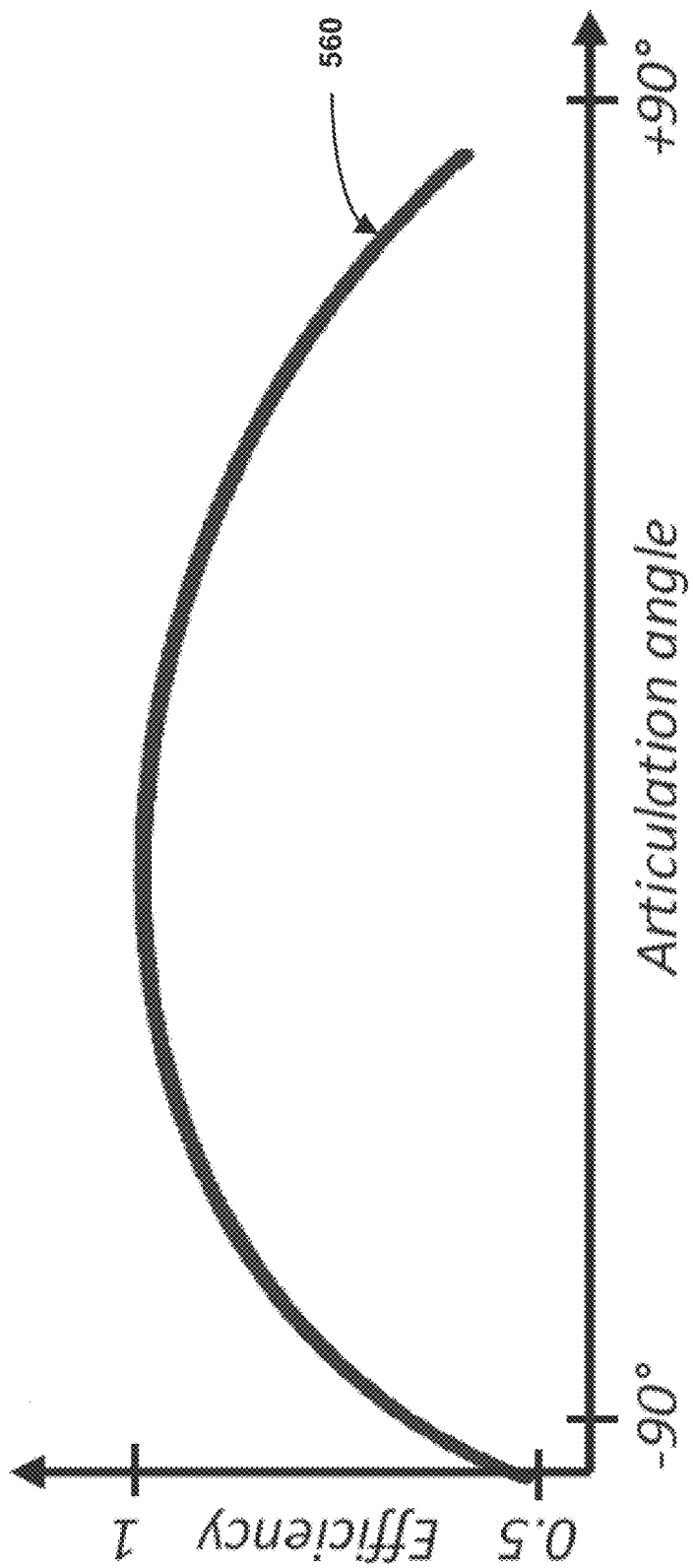
FIG. 5 depicts an illustration of an efficiency plot 500 corresponding to the articulation of the crossed-arm linkage 200, according to an example implementation.

Moreover, as the angle that the pull wire makes with the arm may change throughout the range of articulation, in some implementations, there may be a non-linearity in the efficiency of the transmission between the pull wire and the arm, as shown in FIG. 5.

FIG. 5 depicts an illustration of an efficiency plot 500 corresponding to the articulation of the crossed-arm linkage 200, according to an example implementation. As shown in FIG. 5, the plot of transmission efficiency 560 may follow a parabolic curve. With a fixed point of contact between each arm and pull wire, linkage 600 may also be subject to a similar transmission curve. Accordingly, a third crossed-arm linkage 900 was provided to address these aspects.

Figure 9:
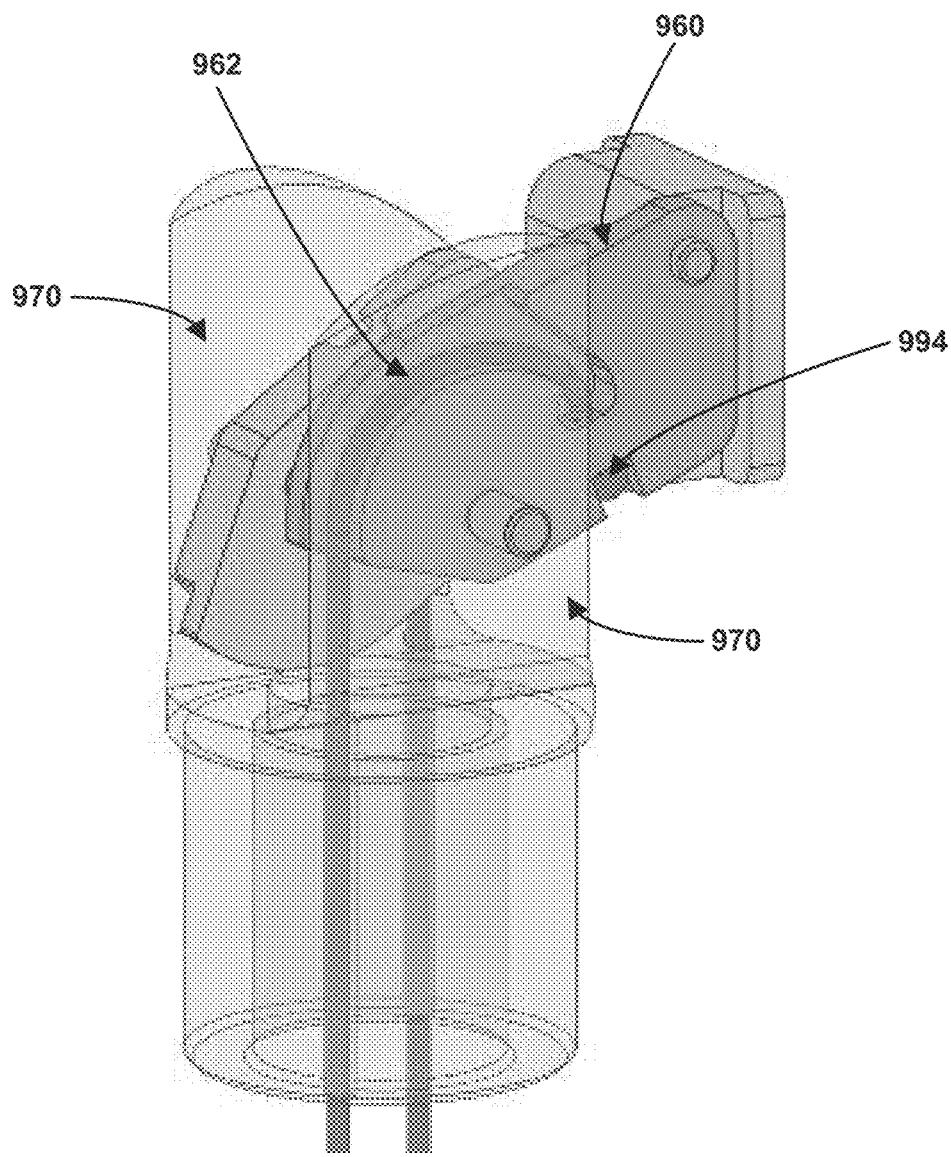
FIG. 9 depicts an illustration of yet another cross-armed linkage 900, according to an example implementation.

FIG. 9 depicts an illustration of yet another cross-armed linkage 900, according to an example implementation. As shown in FIG. 9, pull wire 962 may contact and go around a semicircular feature 964 of arm 960 that acts as a partial pulley. In some implementations, an axis of the partial pulley may be concentric with a respective proximal hinge. In some implementations, the pull wire may be attached at a ball ending resting in a bore 994.

Figure 10A:
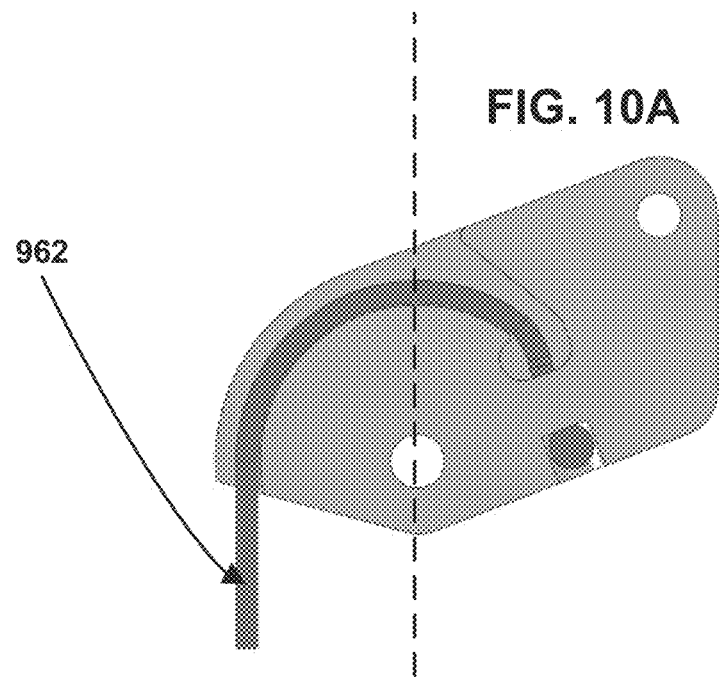
FIGS. 10A and 10B depict illustrations of a platform arm being articulated by a pull wire, according to an example implementation.
Figure 10B:
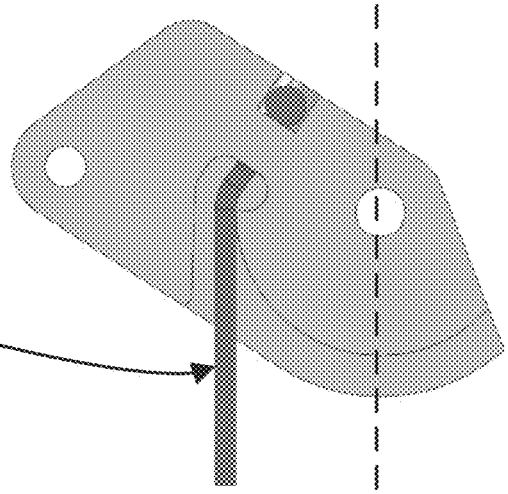
Figure 11:
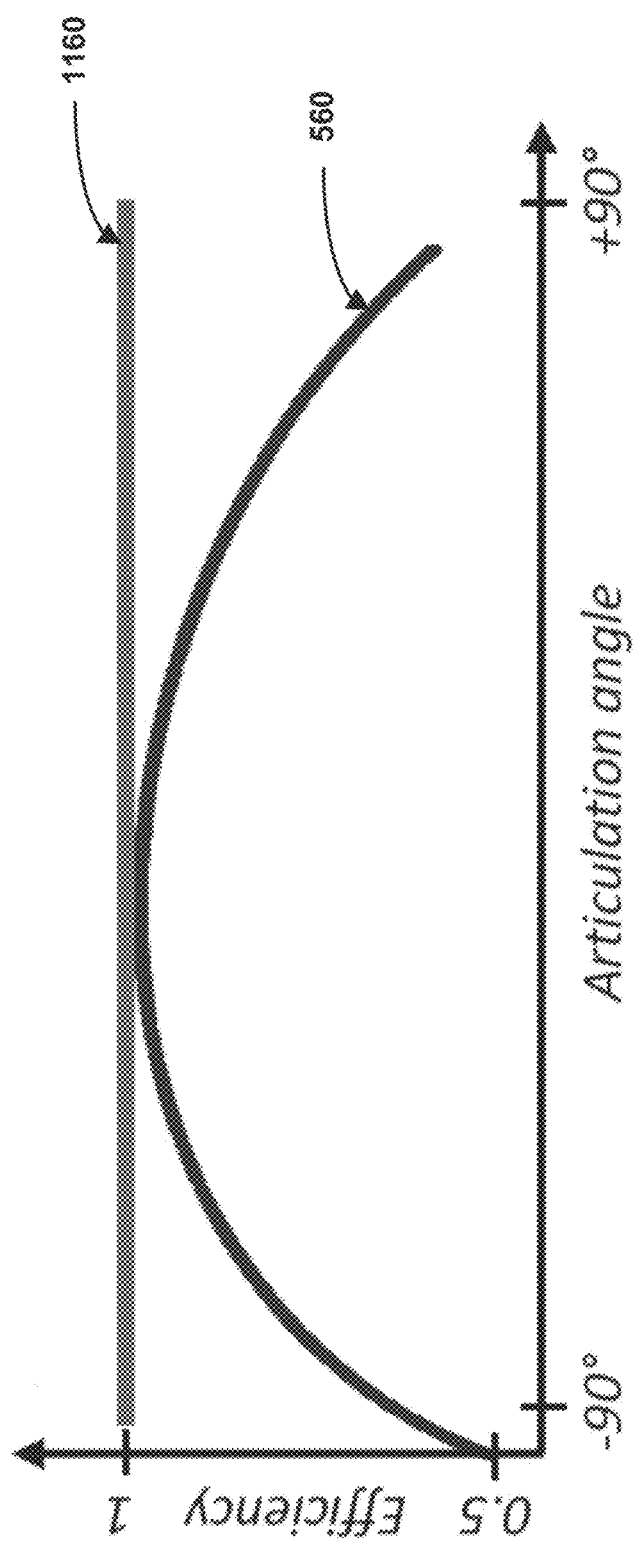
FIG. 11 depicts an illustration of an efficiency plot 1100 corresponding to the articulation of the crossed-arm linkage of 600, according to an example implementation.

FIGS. 10A and 10B depict illustrations of a platform arm being articulated by a pull wire, according to an example implementation. As shown, the pull wire 962 may now stay parallel to the shaft of the tool or perpendicular to a base of the arms. As shown in the updated efficiency plot of FIG. 11, the second plot of transmission efficiency 1160 corresponding to linkage 900 may be constant.

Figure 12:
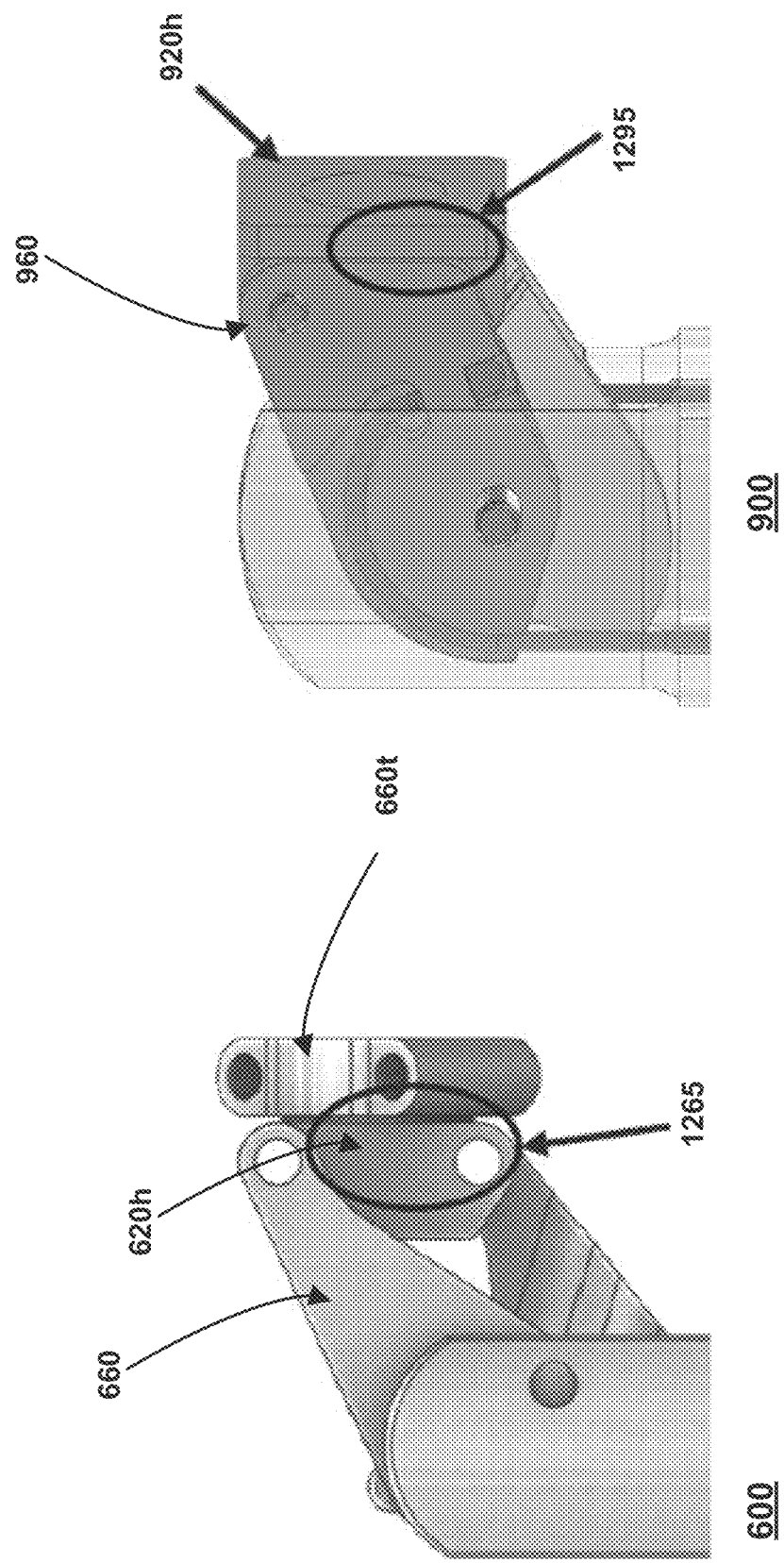
FIG. 12 depicts an illustration of the difference in arm to platform overlap between linkages 600 and 900.

Other advantages of linkage 900 may include reduced parts, as the pierced pin may be omitted, and shorter base walls 970, which may increase the structural stiffness of the implementation. Moreover, the different shape of the extremity of the arms 960 may provide another pressure point to add torsional stiffness to the head. FIG. 12 depicts an illustration of the difference in arm to platform overlap between linkages 600 and 900. As shown in FIG. 12, arm 860 of linkage 600 may not significantly overlap 1265 the head 820h of the platform assembly, however arm 1260 of linkage 900, does significantly overlap 1295 the head 1220h of the platform assembly.

In another implementation, the pins attaching the arms to the head of the platform assembly may be lengthened so that they protrude from the sides of the head. This may prevent the head from popping out when torque or lateral force is applied.

According to many implementations, an end effector of the surgical tool may be a grasper, as shown in FIG. 1. Various grasper configurations were evaluated with the goals of reducing a radial offset of the tool while providing at least 30° of articulation and improved grip strength and scalability.

Figure 14B:
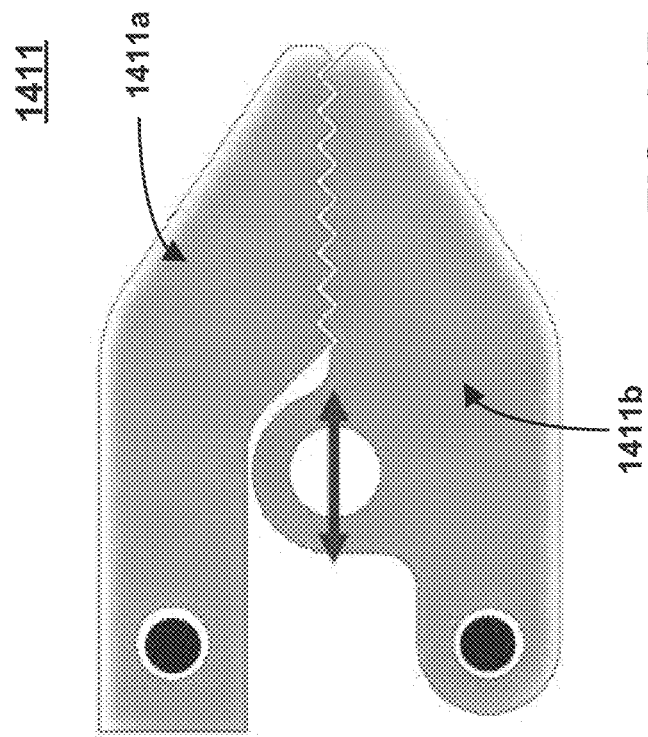
FIG. 14B depicts an illustration of a unilateral grasper 1411, according to an example implementation.

FIGS. 15A and 15B depict illustrations of a deformable grasper, according to an example implementation. A compliant or deformable grasper relies on elastic properties of the material to deform and return back into its initial shape, in contrast to a rigid grasper, as shown in FIGS. 14A and 14B.

In some implementations, a mode of operation of the deformable grasper may involve actuating the closing of the grasper by pulling on face 1560. This may then cause the jaws to collapse onto each other, for example to grab tissue or a needle. In another implementation, the default position of the jaws may be closed and the grasper may deform to open under stress.

According to many implementations, due to energy stored in the grasper during the elastic deformation, the grasper may return to a default position without additional force from the wire. In some implementations, the actuation maybe effected by a tensionable or pushable wire, which may be disposed within a torque coil, as described herein.

Figure 14A:
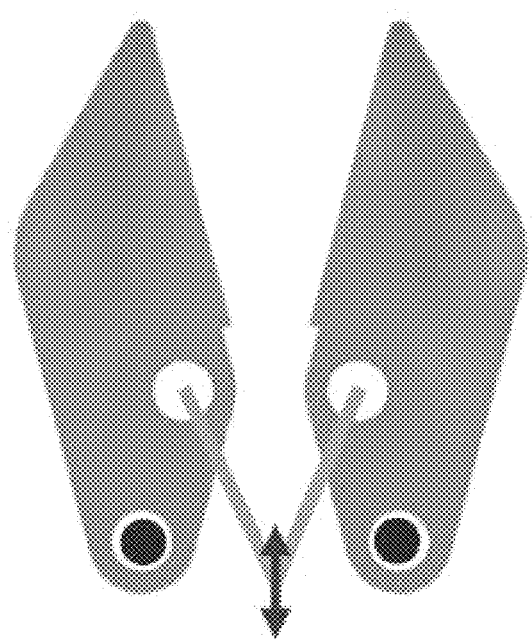
FIG. 14A depicts an illustration of a bilateral grasper 1410, according to an example implementation.

FIG. 14A depicts an illustration of a bilateral grasper 1410, according to an example implementation. FIG. 14B depicts an illustration of a unilateral grasper 1411, according to an example implementation. Both the bilateral and unilateral grasper may require both push and pull actuation in order to open and close.

An advantage of bilateral grasper 1410 may lie in having symmetrical jaw behavior throughout articulation. Thus, it may be relatively easier and intuitive for an operator to grasp a targeted tissue.

A unilateral grasper 1411 may have less moving parts than a bilateral grasper, and the fixed jaw 1411a may be used in additional ways such scooping under tissue or providing a stiff terminal end to prod objects. Although, it may be more difficult for an operator to grasp a target tissue with a unilateral grasper due to the asymmetry, in some implementations, by rolling the grasper articulation range to align with the pitch DOF, software may help maintain the position of a centerline between the jaws 1411a and 1411b so as to make grasping a target tissue more intuitive.

Figure 16:
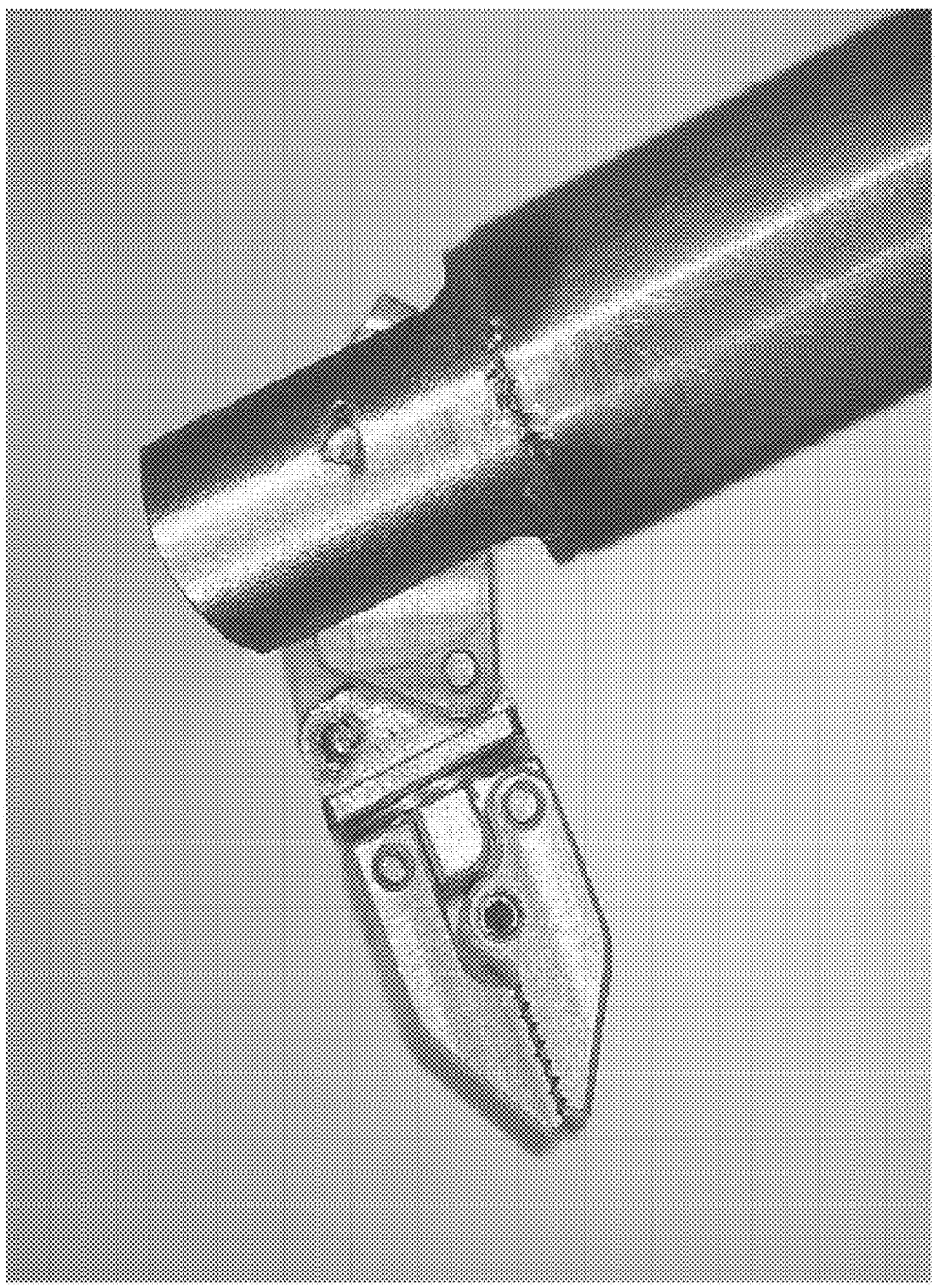
FIG. 16 depicts an illustration of a microsurgical tool 1600 incorporating linkage 900, according to an example implementation.
Figure 17:
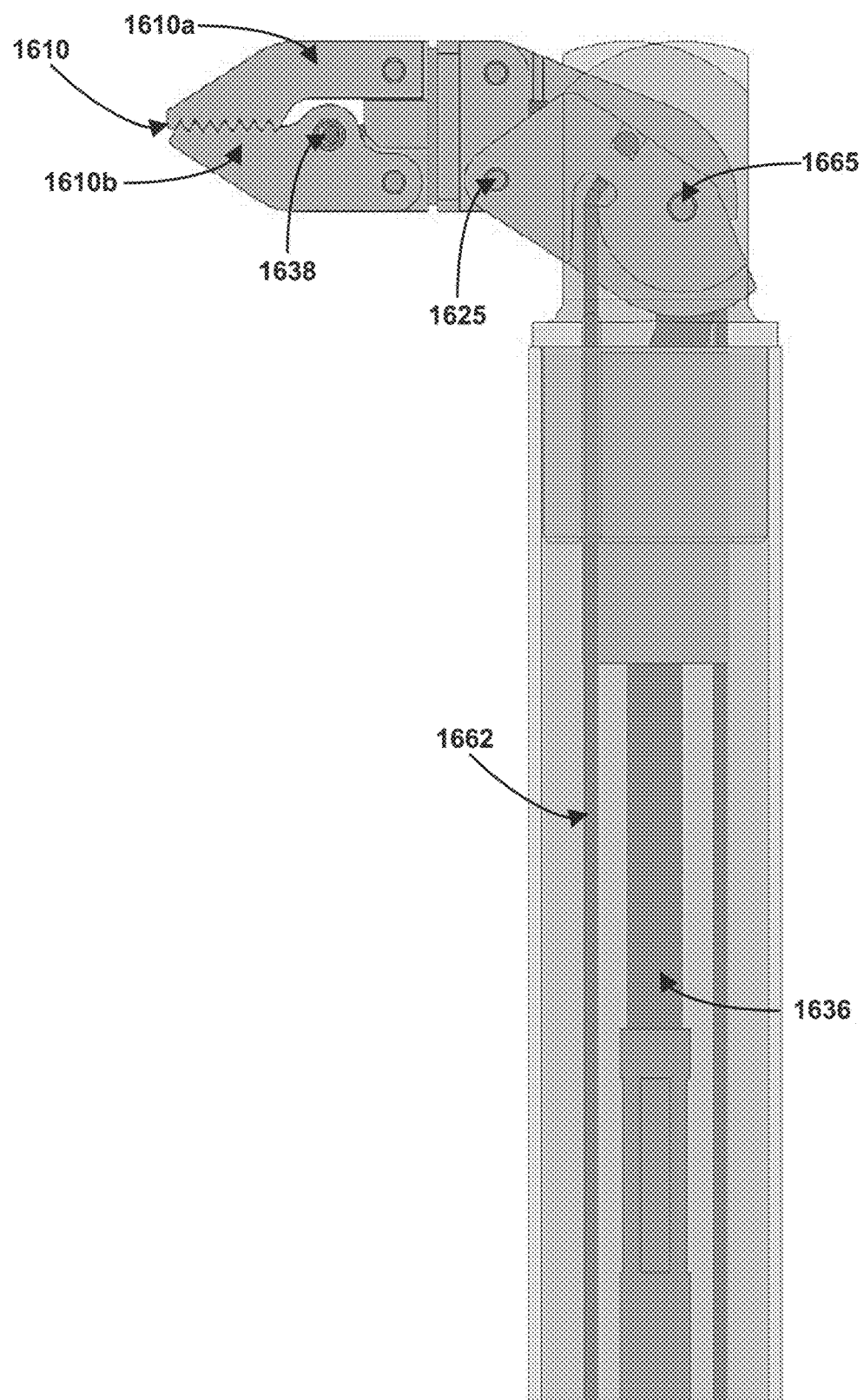
FIG. 17 depicts an illustration of a first profile of the microsurgical tool 1600, according to an example implementation.
Figure 18:
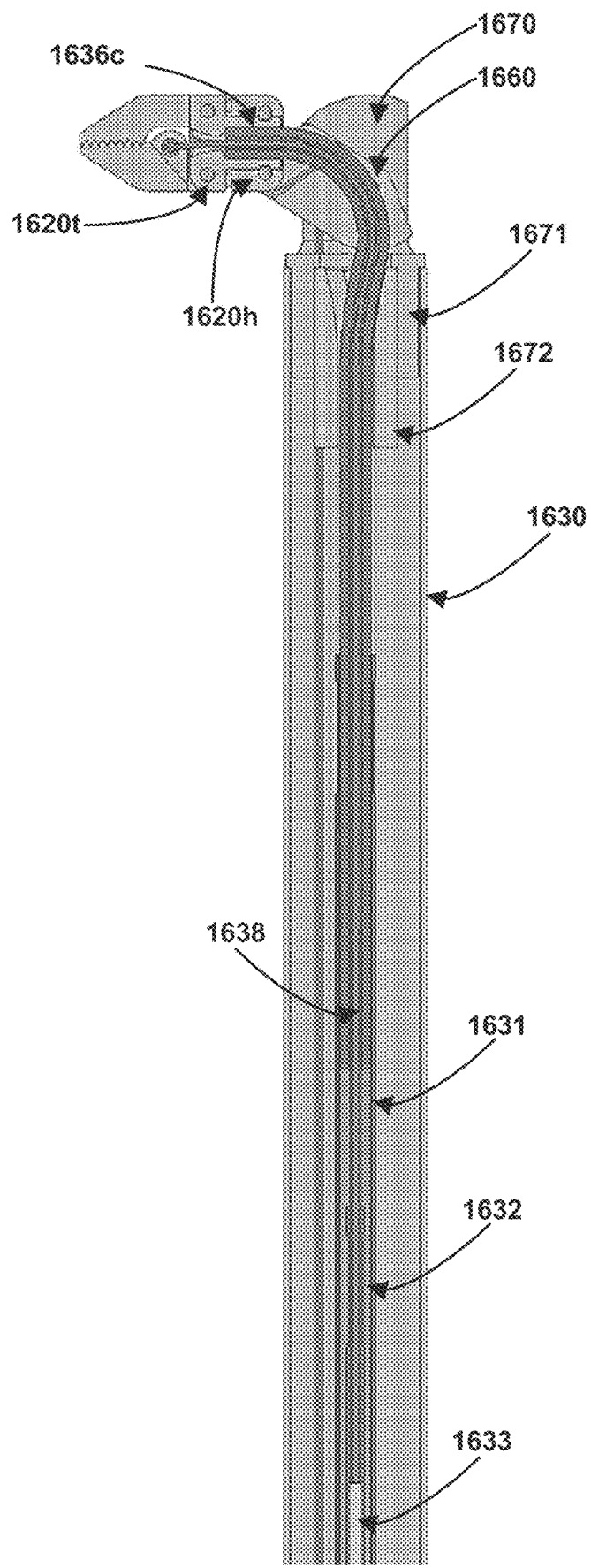
FIG. 18 depicts an illustration of a second profile of the microsurgical tool 1600, according to an example implementation.

FIG. 16 depicts an illustration of a microsurgical tool 1600 incorporating linkage 900, according to an example implementation. As shown in FIGS. 17-18, the example microsurgical tool comprises a shaft 1630 moveably coupled to a platform assembly including tip 1620t and head 1620h. The shaft has an outside diameter of 5 mm. The shaft and platform assembly are linked by hinged arms 1660 based on crossed-arm linkage 900. Each arm is coupled to the shaft at a respective proximal hinge 1665 and to the head at a respective distal hinge 1625. Each arm is operated by a respective pull wire 1662 routed over a semi-circular portion of each respective arm that acts as a partial pulley.

A unilateral grasper 1610 is mounted at the tip of the platform assembly. The radial offset of the grasper is 6 mm, giving the tool a ratio of outside diameter to radial offset of 0.83. The grasper has a fixed jaw 1610a and a moveable jaw 1610b. The grasper is operated by grasper tendon 1638 made of nitinol and allowing the jaws to open more than 30° and close. The tendon is piped through a torque coil 1636, with both the tendon and torque coil disposed within an inner diameter of the shaft. The torque coil transmits force for rotating the grasper in a roll DOF.

A 6TW hypotube was used for the shaft. Within the shaft are several other layers of hypotube including a 17.5 GA hypotube 1631, 27 W hypotube 1632, and 23 TW hypotube 1633. Base walls 1670, base support 1671, and base core 1672 provide support for the torque coil and add stiffness to the tool.

While preferred embodiments of the present technology have been shown and described herein, it will be obvious to those skilled in the art that such embodiments are provided by way of example only. Numerous variations, changes, and substitutions will now occur to those skilled in the art without departing from the technology. It should be understood that various alternatives to the embodiments of the technology described herein may be employed in practicing the technology. It is intended that the following claims define the scope of the technology and that methods and structures within the scope of these claims and their equivalents be covered thereby

What is claimed is:

1. A microsurgical tool, comprising:
   an elongated body having a distal end;
   a platform moveably coupled to the distal end of the elongated body; and
   a linkage coupling the distal end of the elongated body to the platform to allow the platform to move relative thereto, wherein the linkage comprises:
      a first arm directly operatively coupled to the distal end of the elongated body at a first proximal hinge and to the platform at a first distal hinge, the first arm having a first redirect surface,
      a first force transfer element disposed around the first redirect surface before terminating at the first arm such that pulling the first force transfer element pivots the first arm about the first proximal hinge with a first amplified range of motion,
      a second arm directly operatively coupled to the distal end of the elongated body at a second proximal hinge and to the platform at a second distal hinge, the second arm having a second redirect surface, and
      a second force transfer element disposed around the second redirect surface before terminating at the second arm such that pulling the second force transfer element pivots the second arm about the second proximal hinge with a second amplified range of motion.

2. The microsurgical tool of claim 1, wherein the first and second arms are crossed with respect to one another.

3. The microsurgical tool of claim 1, wherein the first and second arms form a mechanical linkage for moving the first arm with a constant transmission efficiency between the mechanical linkage and the first arm throughout a range of movement of the first arm.

4. The microsurgical tool of claim 1, wherein the first and second amplified ranges of motion are of the same magnitude in opposite directions.

5. The microsurgical tool of claim 1, wherein the first proximal hinge and the second proximal hinge are co-axial.

6. The microsurgical tool of claim 1, wherein the first distal hinge and the second distal hinge are coupled to diametrically opposite positions on the platform.

7. The microsurgical tool of claim 1, wherein the first force transfer element comprises a pull wire.

8. The microsurgical tool of claim 1, wherein the first force transfer element and the first redirect surface of the first arm form a partial pulley to provide the first amplified range of motion.

9. The microsurgical tool of claim 1, wherein the first amplified range of motion is in a pitch degree of freedom.

10. The microsurgical tool of claim 1, wherein the first redirect surface of the first arm comprises a first semicircular portion.

11. The microsurgical tool of claim 10, wherein the first semicircular portion is concentric with the first proximal hinge.

12. The microsurgical tool of claim 1, wherein the first force transfer element is coupled to a first bore of the first arm, wherein the first bore is offset from a first line formed between the first proximal hinge and the first distal hinge.

13. The microsurgical tool of claim 1, further comprising an end effector operatively coupled to the platform.

14. The microsurgical tool of claim 13, wherein the end effector comprises a grasper.

15. The microsurgical tool of claim 13, wherein the end effector comprises at least one jaw, and further comprising a first tendon coupled to the at least one jaw and tensionable to move the at least one jaw, providing the at least one jaw with a grasping degree of freedom.

16. The microsurgical tool of claim 15, wherein the tendon is disposed at least partially within the elongated body.

17. The microsurgical tool of claim 13, further comprising a torque coil operatively coupled to the end effector to provide the end effector with a roll degree of freedom.

18. The microsurgical tool of claim 17, wherein one or more of the elongated body and the platform comprise a channel through which the torque coil is disposed.

19. The microsurgical tool of claim 1, wherein the elongated body has a centerline, and wherein the first proximal hinge is offset from the centerline.

20. A microsurgical tool, comprising:
    an elongated body having a distal end;
    a platform moveably coupled to the distal end of the elongated body; and
    a linkage coupling the distal end of the elongated body to the platform to allow the platform to move relative thereto, wherein the linkage comprises:
       a first arm directly operatively coupled to the distal end of the elongated body at a first proximal hinge and to the platform at a first distal hinge, the first arm having a first redirect surface,
       a first pull wire disposed around the first redirect surface before terminating at the first arm such that pulling the first pull wire pivots the first arm about the first proximal hinge with a first amplified range of motion,
       a second arm directly operatively coupled to the distal end of the elongated body at a second proximal hinge and to the platform at a second distal hinge, the second arm having a second redirect surface, and
       a second pull wire disposed around the second redirect surface before terminating at the second arm such that pulling the second pull wire pivots the second arm about the second proximal hinge with a second amplified range of motion.

* * * * *